US010542922B2

United States Patent
Sia et al.

(10) Patent No.: US 10,542,922 B2
(45) Date of Patent: Jan. 28, 2020

(54) FLUID EXTRACTION AND DRUG DELIVERY SYSTEM AND METHODS USING MICRONEEDLES

(71) Applicant: The Trustees of Columbia University in the City of New York, New York, NY (US)

(72) Inventors: Samuel K. Sia, New York, NY (US); Nalin Tejavibulya, New York, NY (US)

(73) Assignee: THE TRUSTEES OF COLUMBIA UNIVERSITY IN THE CITY OF NEW YORK, New York, NY (US)

( * ) Notice: Subject to any disclaimer, the term of this patent is extended or adjusted under 35 U.S.C. 154(b) by 1056 days.

(21) Appl. No.: 14/779,556

(22) PCT Filed: Mar. 26, 2014

(86) PCT No.: PCT/US2014/031911
§ 371 (c)(1),
(2) Date: Sep. 23, 2015

(87) PCT Pub. No.: WO2014/160804
PCT Pub. Date: Oct. 2, 2014

(65) Prior Publication Data
US 2016/0029937 A1    Feb. 4, 2016

Related U.S. Application Data

(60) Provisional application No. 61/945,684, filed on Feb. 27, 2014, provisional application No. 61/805,450, filed on Mar. 26, 2013.

(51) Int. Cl.
*A61B 5/00* (2006.01)
*A61B 5/15* (2006.01)
(Continued)

(52) U.S. Cl.
CPC ...... *A61B 5/150984* (2013.01); *A61B 5/1459* (2013.01); *A61B 5/14546* (2013.01);
(Continued)

(58) Field of Classification Search
CPC ..... A61B 5/685; A61B 5/1459; A61B 5/1455; A61B 5/14514; A61B 5/150343;
(Continued)

(56) References Cited

U.S. PATENT DOCUMENTS 6,312,612 B1    11/2001    Sherman et al.
7,344,499 B1    3/2008     Prausnitz et al.
(Continued)

FOREIGN PATENT DOCUMENTS

WO    2006116242 A3    12/2007
WO    2009140735 A1    11/2009
(Continued)

OTHER PUBLICATIONS

Li et al., "An optimized hollow microneedle for minimally invasive blood extraction," Biomedical Microdevices, Jul. 26, 2012, vol. 15(1), pp. 17-25.
(Continued)

*Primary Examiner* — Max F Hindenburg
(74) *Attorney, Agent, or Firm* — Potomac Law Group, PLLC; Mark Catan

(57) ABSTRACT

Devices systems and methods for fluid extraction and delivery to human or animal hosts are described. In embodiments, microneedles are employed to provide low infection risk and painless access to and administration of fluids. The disclosed embodiments address, among others, issues of cost, portability, ease of use in remote settings including use by untrained personnel, and others.

23 Claims, 11 Drawing Sheets

(51) Int. Cl.
*A61M 37/00* (2006.01)
*A61B 5/145* (2006.01)
*A61B 5/1459* (2006.01)
*A61B 5/151* (2006.01)
*A61B 5/1486* (2006.01)

(52) U.S. Cl.
CPC ...... *A61B 5/14865* (2013.01); *A61B 5/15003* (2013.01); *A61B 5/1513* (2013.01); *A61B 5/15087* (2013.01); *A61B 5/150099* (2013.01); *A61B 5/15123* (2013.01); *A61B 5/15153* (2013.01); *A61B 5/15163* (2013.01); *A61B 5/150229* (2013.01); *A61B 5/150389* (2013.01); *A61B 5/150503* (2013.01); *A61B 5/150755* (2013.01); *A61B 5/489* (2013.01); *A61B 5/685* (2013.01); *A61M 37/0015* (2013.01); *A61B 5/6831* (2013.01); *A61M 2037/003* (2013.01); *A61M 2037/0023* (2013.01); *A61M 2037/0046* (2013.01); *A61M 2037/0061* (2013.01)

(58) Field of Classification Search
CPC ........ A61B 5/150984; A61M 37/0015; A61M 2037/0061
See application file for complete search history.

(56) References Cited

U.S. PATENT DOCUMENTS

| | | | |
|---|---|---|---|
| 8,303,518 | B2 | 11/2012 | Aceti et al. |
| 8,333,715 | B1 | 12/2012 | Alferness |
| 8,561,795 | B2 | 10/2013 | Schott |
| 8,808,202 | B2 | 8/2014 | Brancazio |
| 8,821,412 | B2 | 9/2014 | Gonzalez-Zugasti et al. |
| 8,827,971 | B2 | 9/2014 | Gonzalez-Zugasti et al. |
| 9,033,898 | B2 | 5/2015 | Chickering, III et al. |
| 9,041,541 | B2 | 5/2015 | Levinson et al. |
| 9,113,836 | B2 | 8/2015 | Bernstein et al. |
| 9,119,578 | B2 | 9/2015 | Haghgooie et al. |
| 2008/0275396 | A1 | 11/2008 | Neerken et al. |
| 2009/0245601 | A1 | 10/2009 | Cohen et al. |
| 2010/0030111 | A1 | 2/2010 | Perriere |
| 2012/0190981 | A1 | 7/2012 | Harris et al. |

FOREIGN PATENT DOCUMENTS

| | | |
|---|---|---|
| WO | 2012125122 A1 | 9/2012 |
| WO | 2012127433 A1 | 9/2012 |

OTHER PUBLICATIONS

Mukerjee et al., "Microneedle array for transdermal biological fluid extraction and in situ analysis," Sensors and Actuators A, Jan. 20, 2004, vol. 114(2-3), pp. 267-275.

Tsuchiya et al., "Development of Blood Extraction System for Health Monitoring System," Biomedical Microdevices, Dec. 1, 2005, vol. 7(4), pp. 347-353.

Wang et al., "Minimally invasive extraction of dermal interstitial fluid for glucose monitoring using microneedles," Diabetes Technology & Therapeutics, Feb. 1, 2005, vol. 7(1), pp. 131-141.

BD Vacutainer Product Brochure [online], [retrieved on Sep. 23, 2015]. Retrieved from the Internet: <URL: http://www.bd.com/vacutainer/hcw_safety/pdfs/brochure.pdf>.

International Search Report and Written Opinion, dated Oct. 8, 2014, for International Application No. PCT/US14/31911.

Seventh Sense Biosystems Product Overview Page [online], [retrieved on Sep. 23, 2015]. Retrieved from the Internet: <URL: http://7sbio.com/products/>.

Extraction

Collection

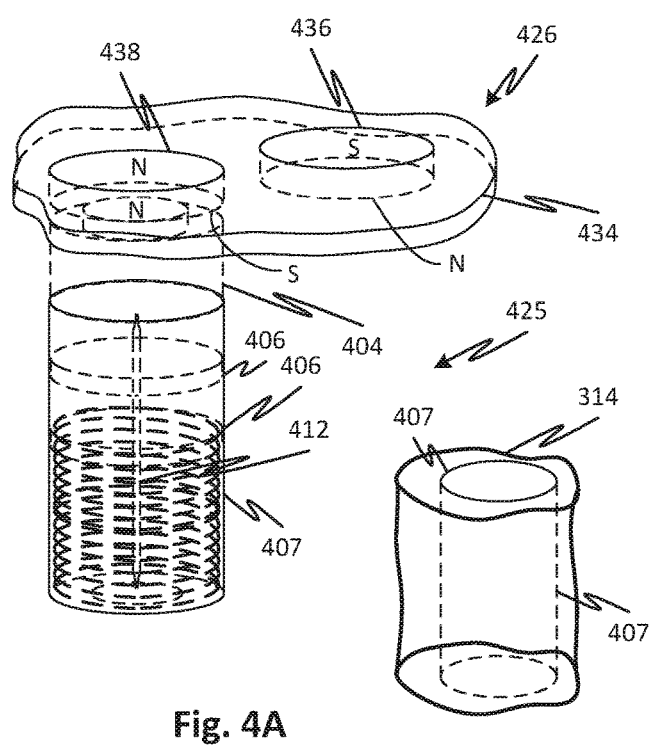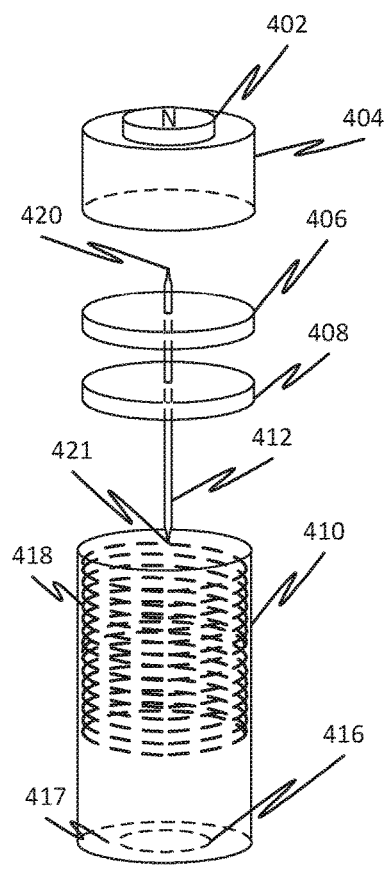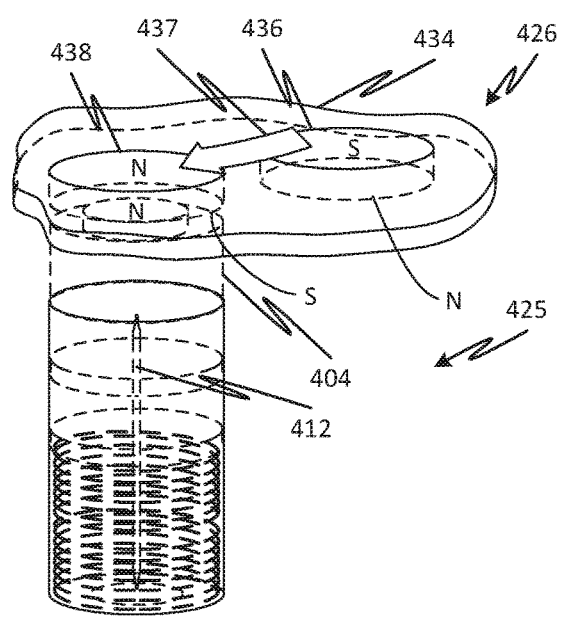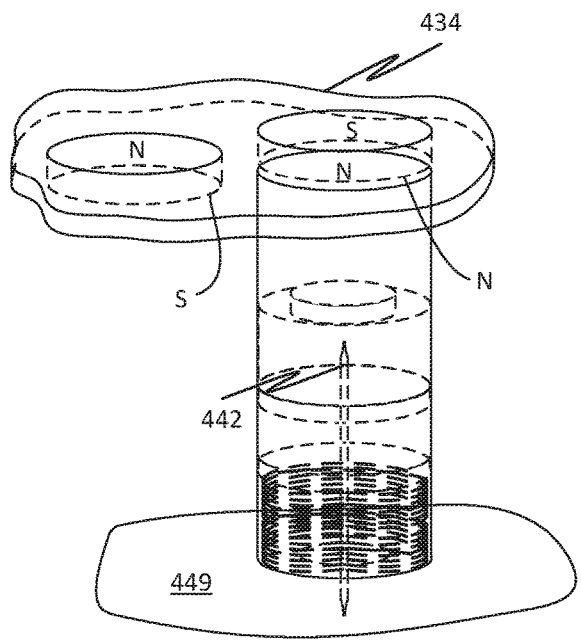
Fig. 4A
Fig. 4E
Fig. 4B
Fig. 4C
Fig. 4D

FLUID EXTRACTION AND DRUG DELIVERY SYSTEM AND METHODS USING MICRONEEDLES

RELATED APPLICATIONS

The present application claims priority to U.S. Provisional Application No. 61/805,450, entitled "Rotary Pump Systems for Microneedles Applied to a Vein," filed Mar. 26, 2013, and U.S. Provisional Application No. 61/945,684, entitled "Fluid Extraction and Drug Delivery Systems and Methods Using Microneedles," filed Feb. 27, 2014, both of which are incorporated herein by reference in their entirety.

FIELD

Embodiments relate generally to devices, systems, and methods for drug administration and fluid extraction from human and animal subjects.

BACKGROUND

A known sample collection is the BD Vacutainer®, used by hospitals for blood sample collection. Benefits include protection against accidental needle sticks. Vacutainer® systems use bottles with prepackaged vacuum stored in them. The vacuum is applied to a needle at the time of sample withdrawal.

Microneedles emulate the efficiency of mosquitos. The mosquito pierces the human skin using its proboscis, which is ~1.5 to 2.0 mm in length. The proboscis consists of two tubes; the labium (inner diameter ~40 μm) and the fascicle (inner diameter ~20 μm), responsible for fluid injection and suction respectively. During the insertion process, through the labium, the mosquito injects saliva, which contains anti-coagulants and also acts as a local anesthetic. The fascicle acts as both a piercing mechanism and a food canal, and draws a volume of ~1-10 μL of blood from the capillary beds at 1500 μm beneath skin surface. On average, it takes a female mosquito about 50 seconds to insert its fascicle into the human skin, and usually around 2.5 min to draw blood at a suction pressure of ~7-8 kPa.

Technologies for fabricating various forms of microneedles are well known. The benefits of painless and safe blood withdrawal and drug administration using microneedles and small gauge needles have been established in demonstration technologies.

SUMMARY

Devices systems and methods for fluid extraction and delivery to human or animal hosts are described. In embodiments, microneedles are employed to provide low infection risk and painless access to and administration of fluids. The disclosed embodiments address, among others, issues of cost, portability, ease of use in remote settings including use by untrained personnel, and others.

Objects and advantages of embodiments of the disclosed subject matter will become apparent from the following description when considered in conjunction with the accompanying drawings.

BRIEF DESCRIPTION OF THE DRAWINGS

Embodiments will hereinafter be described in detail below with reference to the accompanying drawings, wherein like reference numerals represent like elements. The accompanying drawings have not necessarily been drawn to scale. Where applicable, some features may not be illustrated to assist in the description of underlying features.

FIGS. 4A through 4E show an access feature that may be used with any of the embodiments of the disclosed subject matter for sampling fluid from a human or animal host according to embodiments of the disclosed subject matter.

DETAILED DESCRIPTION

It should be understood that the principles described herein are not limited in application to the details of construction or the arrangement of components set forth in the following description or illustrated in the following drawings. The principles can be embodied in other embodiments and can be practiced or carried out in various ways. Also, it is to be understood that the phraseology and terminology used herein is for the purpose of description and should not be regarded as limiting.

Disclosed herein are methods and systems for minimally invasive drug delivery and fluid extraction using microneedles. The disclosed minimally invasive techniques provide ease of use and reduced pain to the subject human or animal subject, enabling self-use while reducing waste.

In certain embodiments of the disclosed subject matter, a system can be used for transdermal fluid extraction, such as blood extraction, from a vein of a human or animal subject. The system can include a hollow micro-needle or array of micro-needles, a pump system such as a rotary pump system, one or more sample storage chambers, and a cap such as a sponge cap.

Figure 1A:
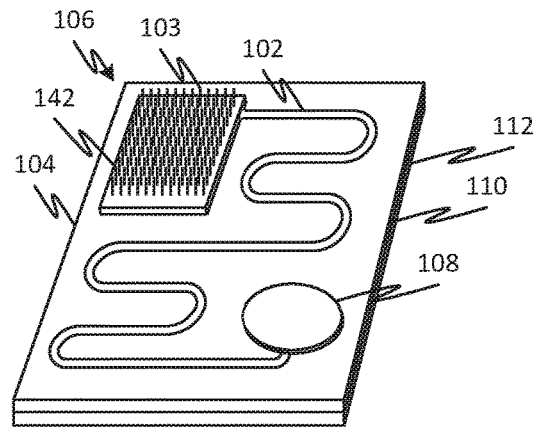
FIG. 1A shows a disposable chip, interoperable with an analysis device, adapted for extracting a biological sample from an animal or human host according to embodiments of the disclosed subject matter.
Figure 1B:
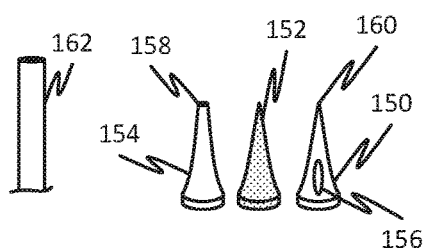
FIG. 1B shows various forms of microneedles that may be used with any of the disclosed embodiments, the configurations being adaptable for use in larger cannulae larger than half a millimeter or even larger, according to embodiments of the disclosed subject matter.

Referring now to FIG. 1A, a chip 104 has fluid passages 102 and a collection chamber 108 which are initially maintained under negative pressure until microneedles 104 of array 106 puncture a film covering them when the microneedles 103 are pressed against the skin of a human or animal subject. Reagents may be distributed within channel 102, which is serpentine to subject fluid flowing therethrough to repeated strain causing mixing of sample and reagent. The sample may be interstitial fluid or blood. The mixed reagent and sample arrives, due to the vacuum, at the sample chamber 108 where it is available for automated or manual inspection. The chip 104 may be shaped to fit into an analysis device, for example, one with an illumination source to cause fluorescence with an optical sensor to permit the quantification of the fluorescent material in the sample chamber 108. The chip may be of manufactured by laminating machined layers to form the channels 102 and chamber 108. The microneedle array may be formed using various different known mechanisms and may have hollow tips or openings remote from the tip. For example, referring to FIG. 1B, microneedle 168 is formed as a silicate glass by stretching in a manner like that for forming optical fibres. The microneedle 168 may be coated with a biocompatible coating such as fluorocarbon film. Other types of microneedles are polymer needles, for example, microneedle 158 with a hollow tip 158, a porous needle 152, and a closed tip 160 needle 150 with one or more openings 156 remote from the tip 160.

Figure 1C:
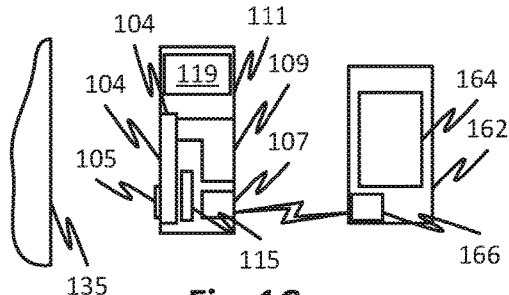
FIG. 1C shows an analysis device and other components including a disposable chip, interoperable with the analysis device, adapted for extracting a biological sample from an animal or human host according to embodiments of the disclosed subject matter.
Figure 1D:
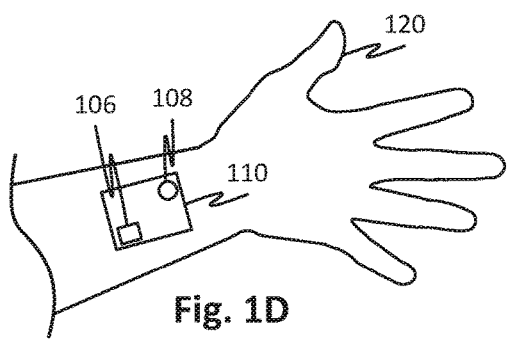
FIG. 1D shows a use case for the embodiments of FIGS. 1A and 1C according to embodiments of the disclosed subject matter.

The chip 104 may be applied to the skin 135 separately from an analysis device or while attached to an analysis device 111 as illustrated in FIG. 1C. See also FIG. 1D illustrating the placement of the device according to a method of use on a body part with blood vessels that are close to the skin. The chip 104 can be applied to any body part, including ones with only capillary blood accessible to the chip 104.

The analysis device 111 may have a pump 115, analysis element 109 which may include analysis components such as a fluorescent source and detector, a wireless transceiver 107, and a receiving portion 113 to allow attachment of the chip 104. The receiving portion 113 may be configured to engage and locate the chip 104 with respect to the other components. If the chip 104 is configured to be used to access the human or animal subject while attached to the analysis device 111, the chip may be provided without a vacuum and a vacuum may be generated by the pump 115 in the analysis device 111 immediately prior to use. In that case, a vacuum tight seal does not need to be maintained except for the duration of a fluid draft.

The analysis device 111 may be provided with a controller 119, such as a digital controller that runs a program to control the pump and analysis devices to draw fluid, perform an analysis and communicate results and other functions to a smart user interface device 162 which may be, for example, a smart phone. The user interface device 162 may have a display 164 and user accessible controls such as a touchscreen (164) as well as a transceiver 166 such as a Bluetooth transceiver. The pump 115 may be a piezoelectric, electromechanical, pure mechanical device. For example, manually or electrically operated syringe with a release control valve controlled by the controller to apply a vacuum to the chip 104.

Figure 1E:
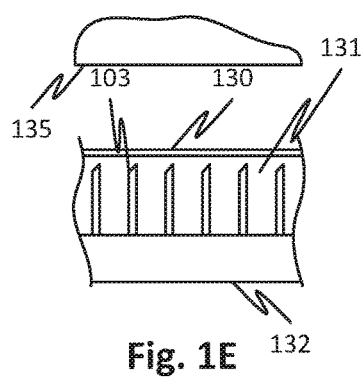
FIGS. 1E and 1F show feature where by a film may employed for vacuum retention and directly pierced by microneedles when used, according to embodiments of the disclosed subject matter.
Figure 1F:
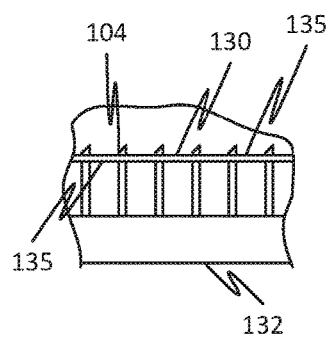

The smart user interface device 162 may include a complete computer that is connectable to the Internet and capable of running programs for data logging, outputting recommendations to users or clinicians, etc. In particular, applications running on the smart user interface device 162 may include programs that are uploaded to the analysis device 111 by the smart user interface device 162 using the wireless link and using the controller 119 to execute them. Applications running on the smart user interface device 162 may also include applications that use diagnostic information on a web site to synthesize and interpret specific diagnostic data from the analysis device 111. Further data from the analysis device 111 transmitted to the smart user interface device 162 may be provided to a server-based web site to be combined with data from other smart user interface devices 162 for statistical analysis and to improve diagnostic information output by the smart user interface device 162. In embodiments, the chip 104 maintains a vacuum within the channel 102 and sample chamber 108. The needles 103 may be sealed against the loss of vacuum by an air impermeable film, for example, a plastic film. In embodiments, the film is a composite film, for example a metallized plastic or multilayer polymer film that is air impermeable. Referring to FIGS. 1E and 1F, in embodiments, a film 130 overlies the microneedle array 106. In embodiments, the film 130 may also be supported by foam layer 131 that is compressible but supports the film under vacuum so that then microneedles 103 do not pierce the film 130. Further the foam 131 may provide some support to the microneedles 103 to keep them oriented. When the array 106 is pressed against the skin 135 of a person, the additional force is sufficient to compress the foam layer 131 to the point that the microneedles 103 can pierce the film 130 while simultaneously piercing the skin 135 and applying a vacuum to draw fluid. In alternative embodiments, the film foam layer 131 is not present and the needles themselves support the film 130 sufficiently to support the maintenance of the vacuum but the film is pierced when the additional pressure of the skin 135 is applied to the tips of the microneedles 104.

Figure 1G:
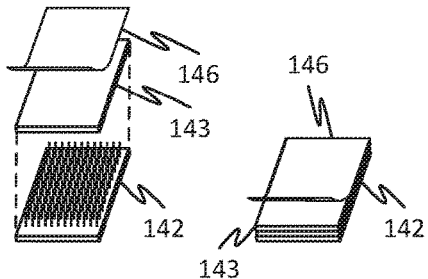
FIGS. 1G and 1H show microneedle array feature of the embodiments in which a foam layer is combined with an impermeable film, according to embodiments of the disclosed subject matter.
Figure 1H:
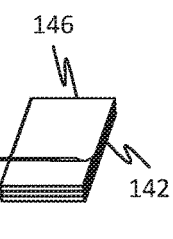

Referring now to FIGS. 1G and 1H, embodiments of microneedle arrays 142 can be covered first by a foam layer 143 which is then covered by an impermeable film 146. Then the channel 102 and sample chamber 108 may be subject to vacuum. The foam and shape of needles as well as the magnitude of the vacuum may be selected to ensure the impermeable film 146 is not pierced by the microneedles of the array 142 before they are applied to the skin of a human or animal subject. In an alternative embodiment, the foam 143 may be selected such that it prevents air from being drawn through the microneedles, for example, a high density closed cell foam. This may be held to the microneedles under the force of vacuum that is insufficient to pierce the foam layer 143. If the tips of the microneedles are below the surface adjacent the film 146, then the force generated by the vacuum tending to pull the needles through the foam layer will be virtually absent. In use, in such an embodiment, the film 146 may be peeled back. The foam layer 143 may be provided with a coating of an anesthetic, antiseptic, and/or anticoagulant which, once exposed, may be applied to the skin before pressing the microneedles array 142 thereagainst causing the needles to pierce through the foam and into the skin.

Figure 1J:
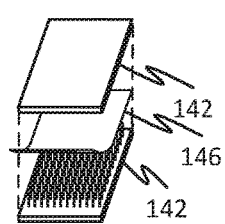
FIGS. 1J and 1K show microneedle array feature of the embodiments in which a foam layer is combined with an impermeable film, according to embodiments of the disclosed subject matter.
Figure 1K:
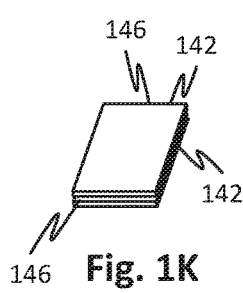
Figure 1L:
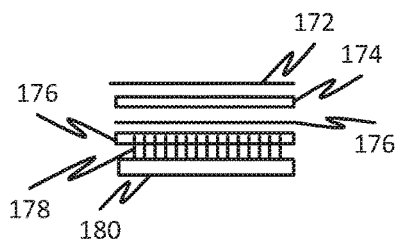
FIG. 1L shows a microneedle array feature of the embodiments in which multiple foam layers are combined with multiple impermeable film layers according to embodiments of the disclosed subject matter.

FIG. 1J shows an embodiment in which an impermeable film 146 is placed over the microneedle array 142 to seal-in the vacuum and a foam later 142 is placed thereover to form the layered arrangement shown in FIG. 1K. In this embodiment, the foam layer can have any of the medicaments mentioned earlier. The film can be pierced by pressure applied during use when the array 142 is pressed against the skin. A further embodiment, shown in FIG. 1L, has two film layers 172 and 176, the layer 172 serving as a protective layer to ensure against the evaporation of fluid (any of the mentioned medicaments) from the foam layer 174 and a barrier film 176 that prevents the loss of vacuum from the chip 180 via the microneedles 178 (arrayed as in the above examples).

Embodiments of further fluid extraction systems according to the present disclosure will now be described. An exemplary embodiment shown in FIGS. 2A-D includes a hollow microneedle or an array of hollow microneedles 205 comprising, e.g., stainless steel, titanium, and/or fiber optics. The microneedles 205 can have a minimum height of 1500 μm, a minimum inner diameter of approximately 60 μm, and an outer diameter of approximately 70-85 μm. The microneedle array 106 may include microneedles in arrays of any form, including irregular arrays, round, rectangular, etc. As discussed above, the microneedles 103 may be of a variety of different forms.

Figure 2A:
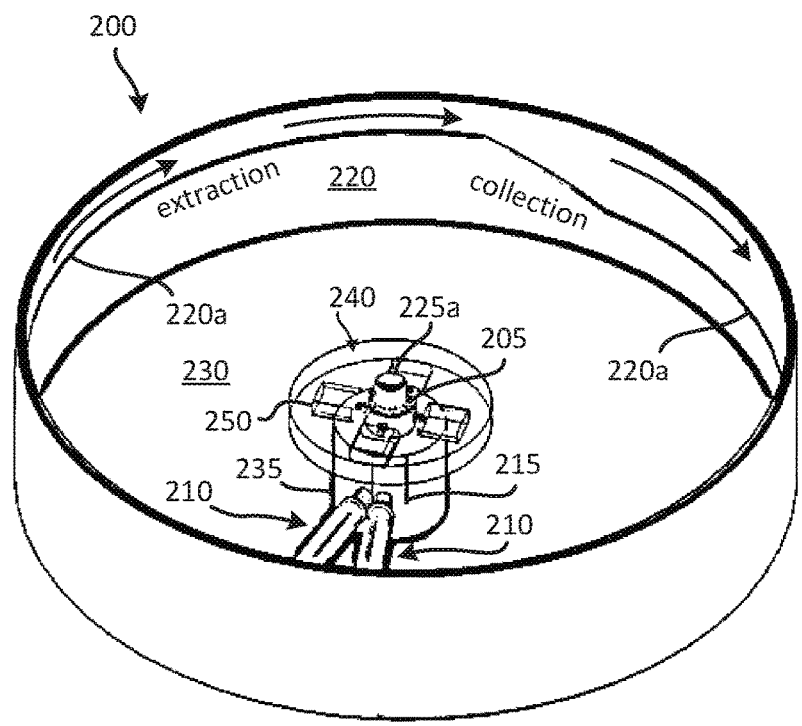
FIGS. 2A through 2D show a fluid extraction system with sample chambers that are configured to pierce the skin of a human or animal subject, draw and store a sample of fluid in sample chambers, and remove the access from the skin in an automated and precise extraction process according to embodiments of the disclosed subject matter.
Figure 2B:
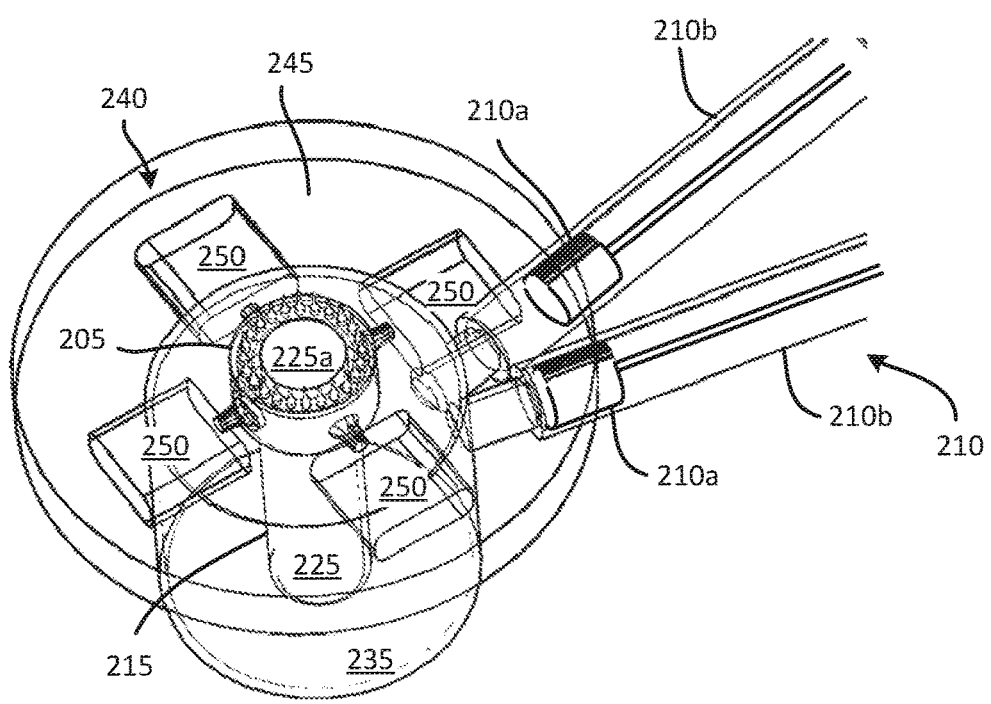

An embodiment of a rotary pump is provided to facilitate the transport of fluid such as blood from a subject's vein, through the microneedle array 205, and into an extraction/collection device. As shown in FIGS. 2A-B, an exemplary rotary pump 200 can include one or more syringe-like cylinder-and-piston sets 210 each attached between two circular tracks; i.e., an inner track 215 nested within an outer track 220, the inner track 215 fixed to be eccentric to the outer track 220. The outer track 220 can be a vertical cylindrical wall, and the inner track 215 can be the periphery of a circular shaft 225 fixed relative to the vertical cylindrical wall 220, such as via a plate 230 attached perpendicularly to the outer track 220. The ends of the pistons 210a can be movably attached to the outer track 220, as by riding in a groove 220a in the track 220, while the inner tips of the cylinders 210b can be attached to a cylindrical sleeve 235 that rotates around the shaft 225 (whose periphery is the inner track 215) and also slides on the shaft 225.

The sleeve 235 is rotatably mounted to a case 240 housing the microneedle array 205 and a collection chip 245, such that a pressure difference generated by action of the piston/cylinder sets 210 can be transmitted to the microneedle array 205 to drive fluid into the case 240 and within the case 240, as by internal passages in the case 240 in a conventional manner. The case 240 of the microneedle array 205 can slide on the shaft 225, so that the end 225a of the shaft 225 can selectively protrude through the middle of the microneedle array 205, as explained in detail below. In certain embodiments, a portion of the shaft 225 proximal the end 225a is splined, and a corresponding portion of case 240 is also splined, to prevent rotation of case 240 about shaft 225 while allowing case 240 to slide on shaft 225. The collection chip 245 can have multiple storage chambers 250. The storage chambers 250 can contain anticoagulants for sample storage, and/or a sensing assay for on-the-spot sample analysis.

In operation, the inner and outer tracks 215, 220 are held stationary against the human or animal subject's skin (not shown). The ends of the pistons 210a are movably engaged with a groove 220a in the outer track 220, the groove 220a having a varying height relative to the plate 230, as shown in FIG. 2A. The assembly including the sleeve 235 and piston/cylinder sets 210 is rotated around the shaft 225 (and the inner track 215) causing the pistons 210a to move within the cylinders 210b, and the sleeve 235 to slide up and down on the shaft 225 as the height of the groove 220a changes. Since the microneedle case 240 is attached to the sleeve 235, it also slides on the shaft 225. Pumping action of the cylinder-and-piston sets 210 is actuated by relative displacements of the pistons 210a as they rotate around the inner track 215, thereby causing a pressure difference to drive fluid into and within the microneedle case 240.

Figure 2C:
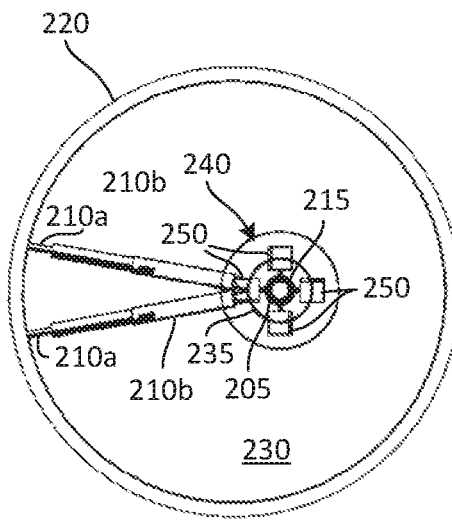
Figure 2D:
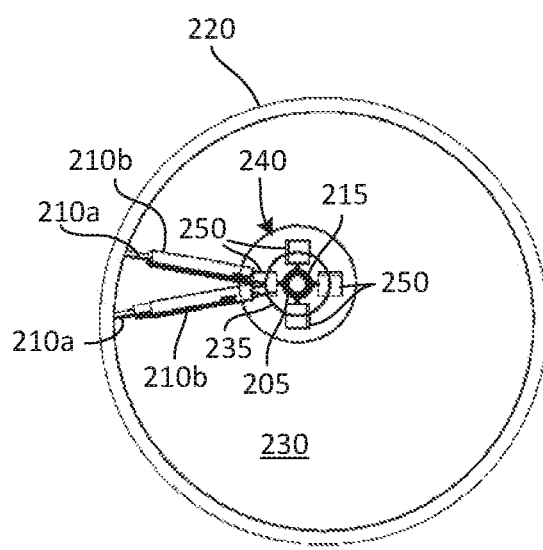

As shown in FIG. 2B, during an extraction mode, the end 225a of the shaft 225 does not protrude through the microneedle case 240, and the microneedles 205 are therefore in contact with the skin (not shown) and fluid can be extracted from the human or animal subject. As shown in FIG. 2C, after about a half a revolution of the sleeve assembly 210, 235, the pistons 210a have been moved to the outer ends of the cylinders 210b, and the extraction process is complete. Referring now to FIGS. 2A and 2D, during a collection mode of operation that follows the extraction mode, the groove 220a in the outer track 220 changes height such that the end 225a of the shaft 225 protrudes through the microneedle case 240, causing the microneedle array 205 to "retract" from the skin. The pistons 210a move to the inner ends of the cylinders 210b, and the collected fluid is moved to the collection chamber(s) 250 of the microneedle case 240.

Thus, the disclosed rotary pump 200 facilitates transport of blood from a human or animal subject's vein into a collection device. The rotary pump system 200 allows active control and manipulation of applied pressure to optimize blood extraction. For example, the varying height of the outer track groove 220a ensures that the microneedle array 205 protrudes out of its case 240 and into the skin only during the extraction cycle, and retracts during the collection cycle, eliminating risk of loss of the sample.

The rotary pump 200 can provide a range of pressure difference; e.g., a minimum of 7 kPa. Its dimensions can be optimized depending on application, but may be dictated by the required pressure difference. The rotary pump system can be constructed of thermosetting plastic such as polystyrene, nylon, polypropylene, or polythene, which can be used in injection molding. Choice of materials can be determined based on material strength necessary for blood extraction applications.

In certain embodiments, the collection chip 245 having one or more sample storage chambers 250 has dimensions providing an overall volume capable of storing, for example, up to 200 μL of blood. The chambers 250 can be spray-coated with anticoagulants; e.g., K2EDTA for immunohematology, silica for immunohematology and diagnostic testing of serum for infectious disease, or lithium heparin or sodium heparin for plasma determinations in chemistry. The sample storage chamber(s) 250 may be in the form of microfluidics channels, and can be constructed with polyethylene terephthalate (PET).

Embodiments of the blood extraction system can further include a cap for covering the microneedle array 205, such as a sponge cap, which may serve to protect and conceal the micro-needles and their sharpness, to apply a fixed dosage of local anesthetic on the extraction site, prior to extraction, and/or to provide mechanical support for the micro-needles during penetration.

In certain embodiments, the disclosed blood extraction system can be integrated with a real-time sensor system, such as an electrochemical glucose sensor system. The system can be easy to use and can provide quick and minimally invasive transdermal extraction of high volumes of blood. Samples retrieved by the system may be stored and used for various diagnostic purposes; for example, disease testing, infectious disease testing, lead testing, coagulation study, blood alcohol testing, blood screening, etc. The disclosed extraction and storage devices may be directly coupled to a diagnostic platform for rapid detection and quantification of specific markers. Additionally or alternatively, embodiments of the disclosed subject matter may be part of a system or device that allows painless self-administered extraction of blood samples; for example, for use as glucose sensors or for point of care diagnostics.

By using a rotary pump system, active control and manipulation of applied pressure to optimize blood extraction can be achieved, as compared to conventional vacuum systems. The rotary pump system can provide a means for the user to actively control the applied pressure to extract blood and allow for the collection volume to be adjusted.

Moreover, the disclosed systems may target veins for blood extraction as opposed to capillaries in the forearm, thereby increasing sample volume over conventional systems. Higher sample volumes ensure that collected samples can be utilized in a wider range of diagnostic applications, to detect both markers present in low and high concentrations. The disclosed systems allow for the collection volume to be controlled within a range of approximately 20-200 μL. The systems can also be configured to collect samples quickly; for example, much faster than the rate of 100 μL in 10 minutes of typical systems. Ten-minute collection times are generally not user-friendly, and can introduce a high chance of clot formation at the needle tip or collection source, reducing the reliability of the system.

Embodiments of the disclosed systems can collect multiple samples and store them in separate compartments. Certain embodiments also allow for multiple samples to be collected at different time points, enabling a change in a marker's concentration over time to be determined. Multiple storage chambers within a single device can contain different preservatives to enhance the preservation of different diagnostic markers.

In certain embodiments of the disclosed blood extraction system, a vein locator, such as an infrared (IR) vein locator, is integrated with the microneedle array to determine the precise location of veins; e.g., veins within 1 cm of the skin's surface. The pump and collection chip can also be integrated with the needle array and IR vein locator. The disclosed system is advantageous because the integration of the microneedles, pump system, and vein locator in one device enables it to be handled with one hand, facilitating self-use by a human or animal subject.

The infrared detection of blood through body tissue is a known technology and details are not elaborated here. For example, US Patent No. 20090245601 to Robert F. Cohen, et. al. describes a system for detecting blood vessels near skin using infrared light by imaging reflected light from the body of a human or animal subject. Illumination of a body part from the surface with infrared light at 880 nm causes high reflection except for blood vessels, containing hemoglobin, which absorb it strongly. By illuminating with light over an area of the skin and measuring the intensity of reflected light at different positions, either using an array of detectors each of which receives light preferentially from a local region or by imaging the reflected light, the positions of blood vessels can be detected relative to a detector. Image sensors capable of detecting light in this range are well-known and readily available, for example, charge coupled devices (CCDs) or complementary metal-oxide semiconductor (CMOS) detectors or imaging chips.

Embodiments of exemplary blood extractor systems with a vein locator according to the present disclosure are presently described. In certain of these embodiments, an array of IR source/photodetector units and microneedles is provided on a rotatable inner ring of a case that also houses electronic components and the pump system. In operation, the array is placed on the arm of the human or animal subject, the IR source/photodetectors determine the target extraction location of a vein, and the inner ring is then automatically rotated to move a microneedle to the target extraction location. In some embodiments, the inner ring rotates to scan the skin area to find the target location. In other embodiments, the inner ring does not scan the skin to find the target location, and the needle that is closest to the target location is determined by the IR source/photodetector units. In each of these embodiments, the selected microneedle is extended into the skin, and the pump system is operated to extract and collect the fluid.

Figure 3A:
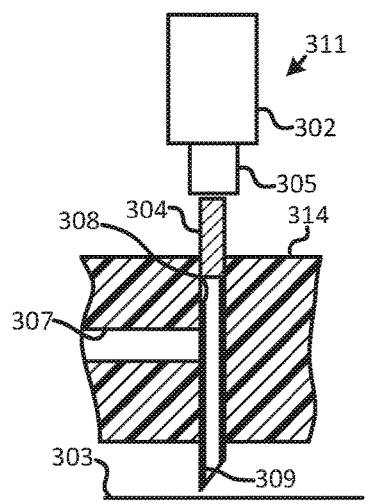
FIG. 3A and 3B shows a cannula or microneedle inserted in a plate with selective connection to a fluid channel which may be used with any of the disclosed fluid extraction system, according to embodiments of the disclosed subject matter.
Figure 3B:
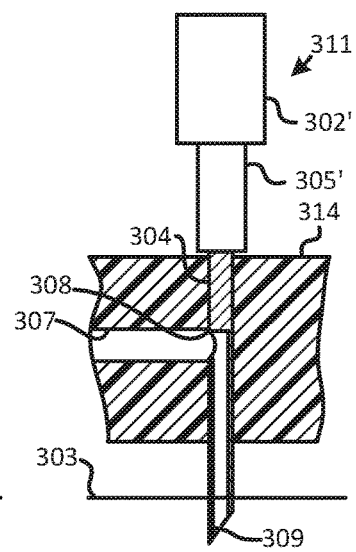
Figure 3D:
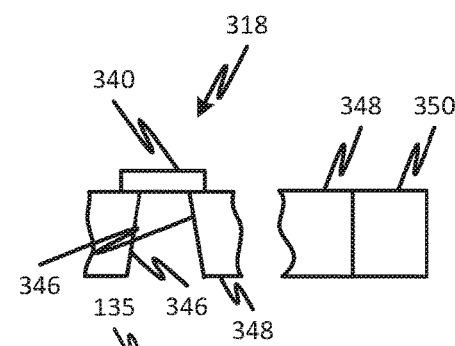
FIG. 3D shows a detector feature that may be used with any of the disclosed blood extraction systems, according to embodiments of the disclosed subject matter.
Figure 3N:
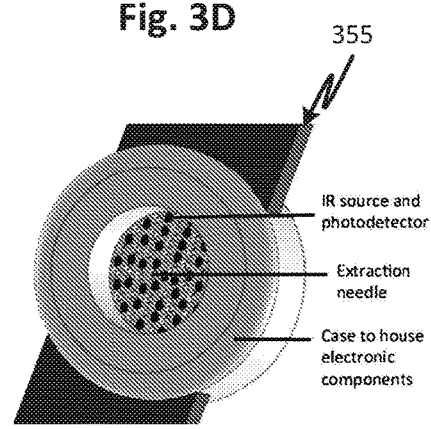
FIG. 3N shows a use case of a blood detector and blood access system according to embodiments of the disclosed subject matter.
Figure 3C:
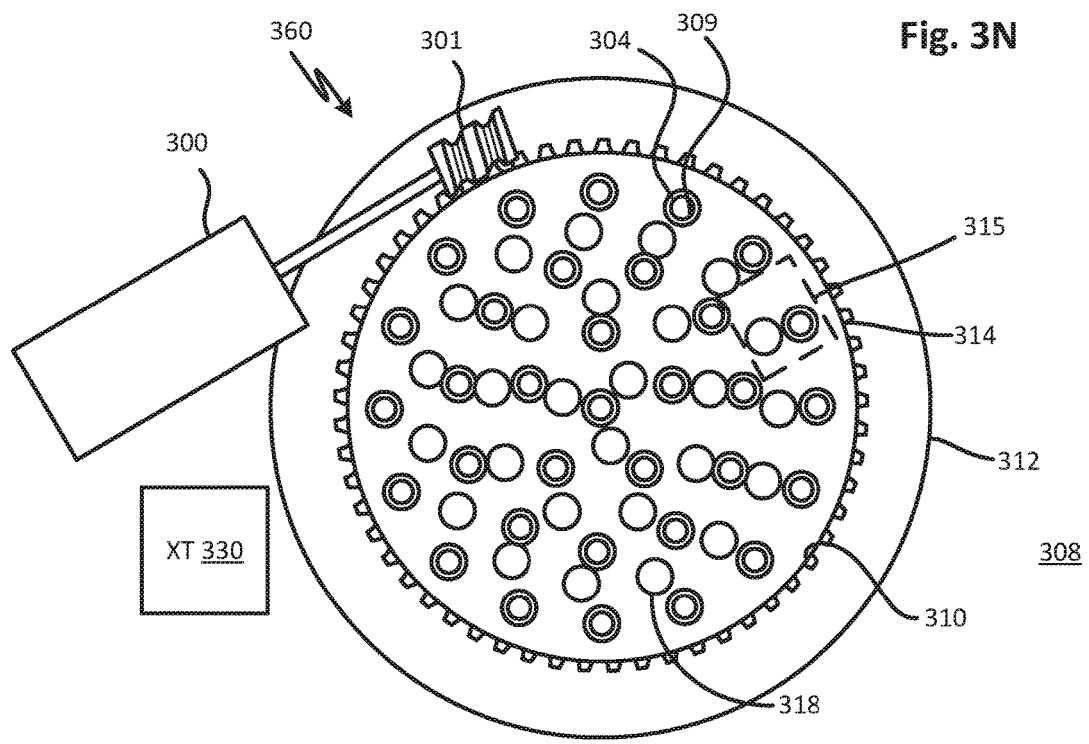
FIG. 3C shows a blood detector and blood access system according to embodiments of the disclosed subject matter.

Referring now to FIGS. 3A to 3C, an embodiment of a blood extractor system 360, with integrated blood locator, is now described. A carrier plate 314, which may be of machined or molded polymer or any other suitable material, as openings for cannulae 304, which may be microneedle-sized or larger (i.e., less than 1000 microns, or less than 500 microns and in embodiments less than 250 microns). In embodiments, the cannulae can be significantly larger, as will be evident from the following description or may have a non-uniform structure permitting the cannula to have a very narrow diameter tip and a strong shaft thereby to permit the cannula to be long enough to allow manufacture and to support the functionality described below. Each cannula 304 has a side opening 308 that, when the cannula 304 is aligned with a channel 307 when the cannula 304 is extended, which places the lumen 309 in fluid communication with the channel 307. The channel 307 is part of a network that may be maintained under vacuum as described below so as to support sample collection. FIGS. 3A and 3B show the cannulae in a retracted and extended position. The cannula 304 may be provided as part of a disposable unit with the cannulae 304 in the retracted position. At a selected time, a particular cannula 304 of may (See FIG. 3B) is extended by a motor 311, here illustrated by a linear motor, for example, a spring motor, a piezoelectric linear drive, a screw drive, hydraulic, pneumatic, or any other suitable mechanism. The motor 311 may be of any type, linear or otherwise. For example, a force may be applied by an expanding bellows a spring-actuated scissor mechanism.

When the cannula 304 is extended, it also pierces the skin 303 of a human or animal subject. In the extended position a vacuum that exists in channel 307 is consequently applied to the lumen 309 of the cannula 304 causing fluid to be drawn through the cannula 304 lumen 309 and into the channel 307. The channel 307 may be in communication with a sample chamber (not shown in the present drawing) such that fluid drawn through the channel 307 is conveyed to the chamber and collected therein. The cannula 304 may be one of a set of cannulae forming an array as described in the following embodiments and shown, for example, in FIG. 3C. The plate 314, which has a toothed edge that engages a screw 301 driven by a motor 300, rotates to place a selected one of a plurality of cannulae into a position indicated by an optical scanner. The optical scanner includes a plurality of infrared sources and detectors, one of each located at each of a plurality of positions (e.g., indicated at 318) spanning the surface of the plate 314. The surface of the plate 314 facing the viewer in the aspect of FIG. 3C faces the skin of a human or animal subject when the blood extractor device 312 is used.

Referring now also to FIG. 3D, a controller 330 is connected to the motor 300, detectors 318, which include infrared sensors 340 and a light sources 346. A single detector 318 is shown in FIG. 3D with a perimeter portion of the plate 348 to which it is attached. A light source 350 transmits light into the plate 348, which is a light guide. The light is transmitted through the light guide plate 348 and exits through an extraction feature provided at surface 346. The surface 346 may also be provided with light reflecting or refracting features that direct light downwardly toward the skin of human or animal subject's skin 135. The light returned from the human or animal subject is received by the sensor 340 as well as other similar sensors and the controller 330 computes a best position for blood extraction based on the signal indicating the distribution of hemoglobin. The controller 330 may compute the relative intensity of the calibration-normalized absorption as indicated by the relative intensity distribution. Since this distribution is known at multiple points arrayed about an area of skin, a low spot may be deemed to coincide with an optimal position. The low spot (high absorption=maximum hemoglobin near surface) may be interpolated to fall at a location that does not coincide with a specific spot. The controller 330 may operate the motor 300 to displace the detectors 318 while acquiring the signal to absorption signal to enhance the resolution of the image of the absorption distribution at least over the range of radii over which the detectors 318 are positioned.

Using the absorption distribution data, the controller may position a cannula 304 at the closest radial and angular position to the peak absorption position by activating and running the motor 300. Then the controller 330 may activate the motor 311 to cause the cannula 304 to penetrate the skin 303 at the closest accessible point while sampling the blood of the animal or human subject in the manner described above with reference to FIGS. 3A and 3B.

The method implemented by the controller 330 may include activating the light source 350 and simultaneously sampling the sensor signals from all the sensors 340 of all the detectors 318. The motor 300 may then be activated to rotate the plate 348 while further samples are acquired and stored. A distribution may then be computed and fitted to a surface function such as a cubic spline. The peak absorption indicated by the surface fit may be identified by the controller. Then the controller may compute the number of rotations, and the direction, of the motor necessary position a cannula 304 which is located at the closest radial and angular position, to position the cannula 304 at the peak absorption position. Then the controller 330 may activate the motor 311 to cause the cannula 304 to penetrate the skin 303 at the closest accessible point while sampling the blood of the animal or human subject in the manner described above with reference to FIGS. 3A and 3B.

In any of the foregoing embodiments, the motor 311 may be replaced with a thermal motor that employs one or more bimetallic (or other materials with differing thermal expansion properties) so as to generate a motive force using heat from a resistive heater. Similarly a shape memory motor employing shape memory materials heated by resistive heater may be used to achieve a low profile to allow the system to be fitted into a watch-sized structure 355. See FIG. 3N.

Figure 3E:
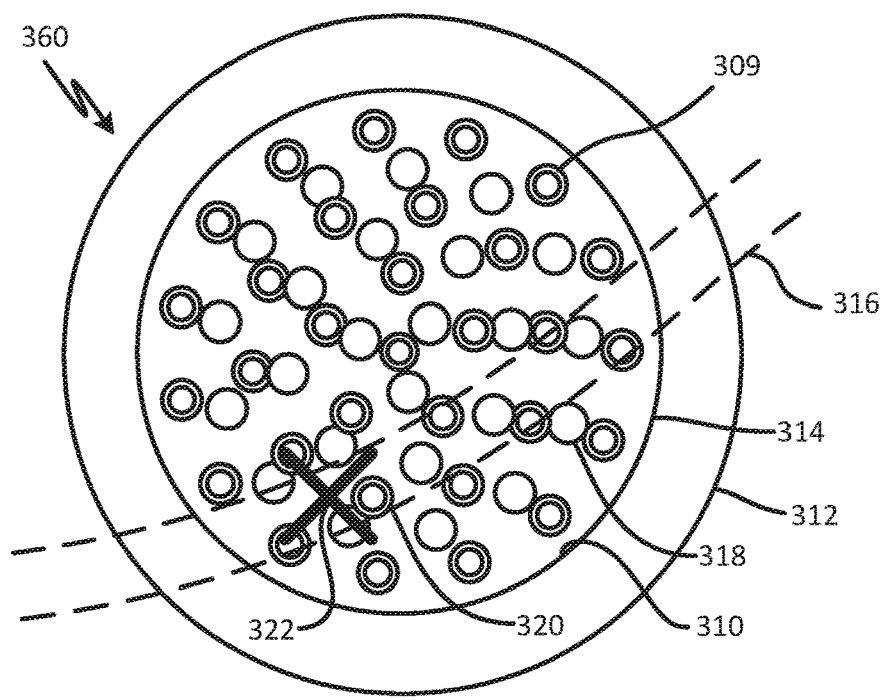
FIGS. 3E and 3F show a partial side/section view of features of the embodiment of FIG. 3D to illustrate functions for positioning a cannula according to embodiments of the disclosed subject matter.
Figure 3F:
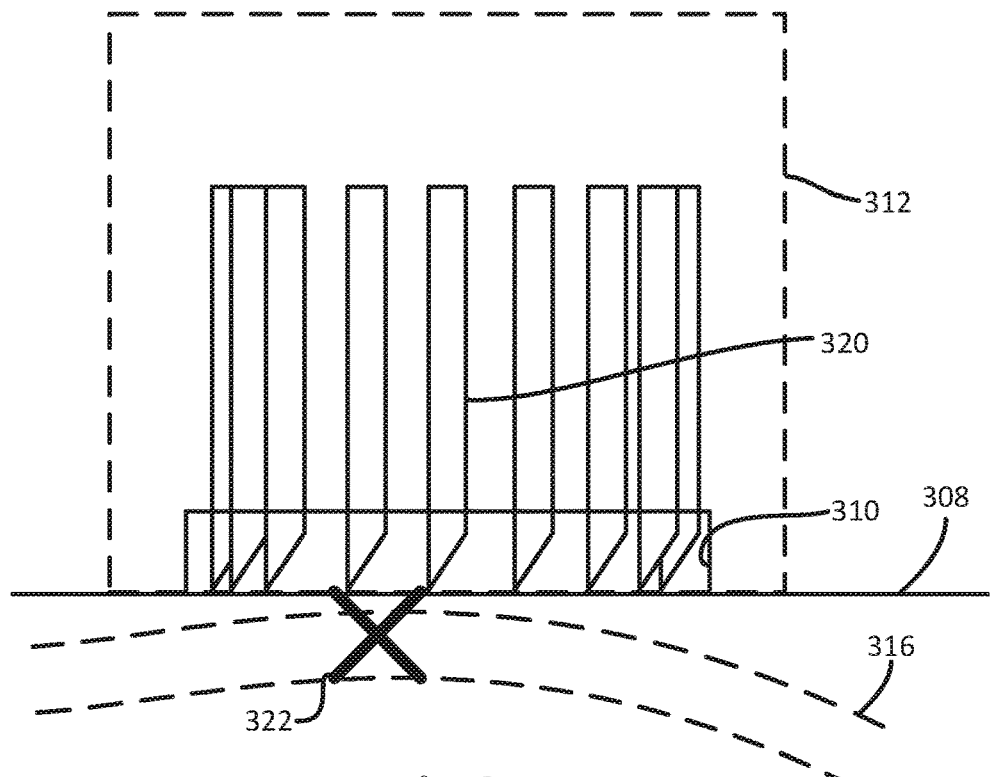
Figure 3G:
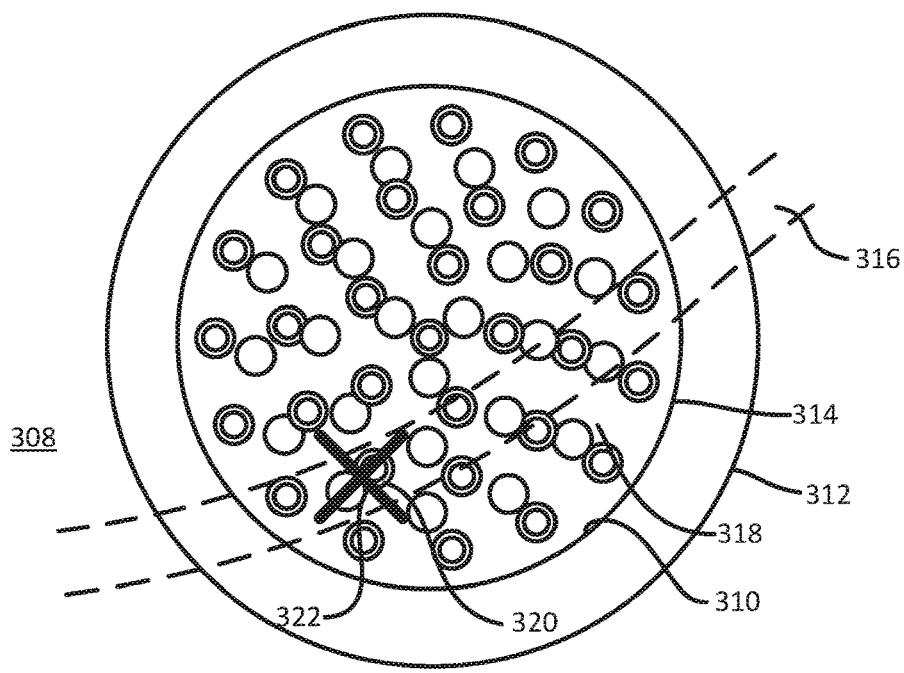
FIGS. 3G and 3H show a partial side/section view of features of the embodiment of FIG. 3D to illustrate functions of inserting a cannula in a human or animal subject, according to embodiments of the disclosed subject matter.
Figure 3H:
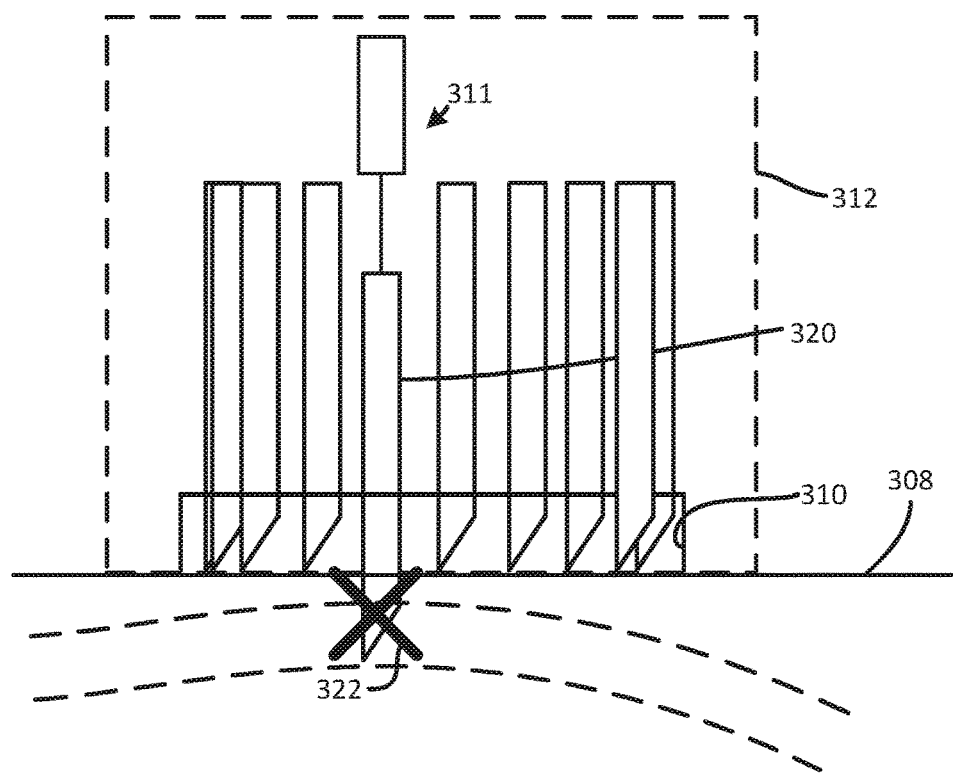

FIGS. 3E and 3F illustrate parts of the blood extractor system 360 with an outline of a blood vessel 316 superimposed thereon. The target location is marked with a large "X." The target location indicated by light absorption results from a combination of the closeness of the blood to the skin 308 (i.e., the position of the blood from the perspective of FIG. 3F) and the position of the blood vessel on the planar projection on a plane parallel to the skin surface (i.e., from the perspective of FIG. 3E). The cannulae selected according to its radial and angular position (clockwise position) is indicated at 320. The motor 300 only has to move the plate 310 far enough to position the selected cannula 320 over the target location X. The elevation of a blood vessel is shown by the outline 322. The casing of the blood extractor system 360 is indicated at 312. FIGS. 3G and 3H show the same views and apparatus as FIGS. 3E and 3F after the cannula 320 has been moved to a position close to the target position X and the motor 311 activated to cause insertion.

Figure 3J:
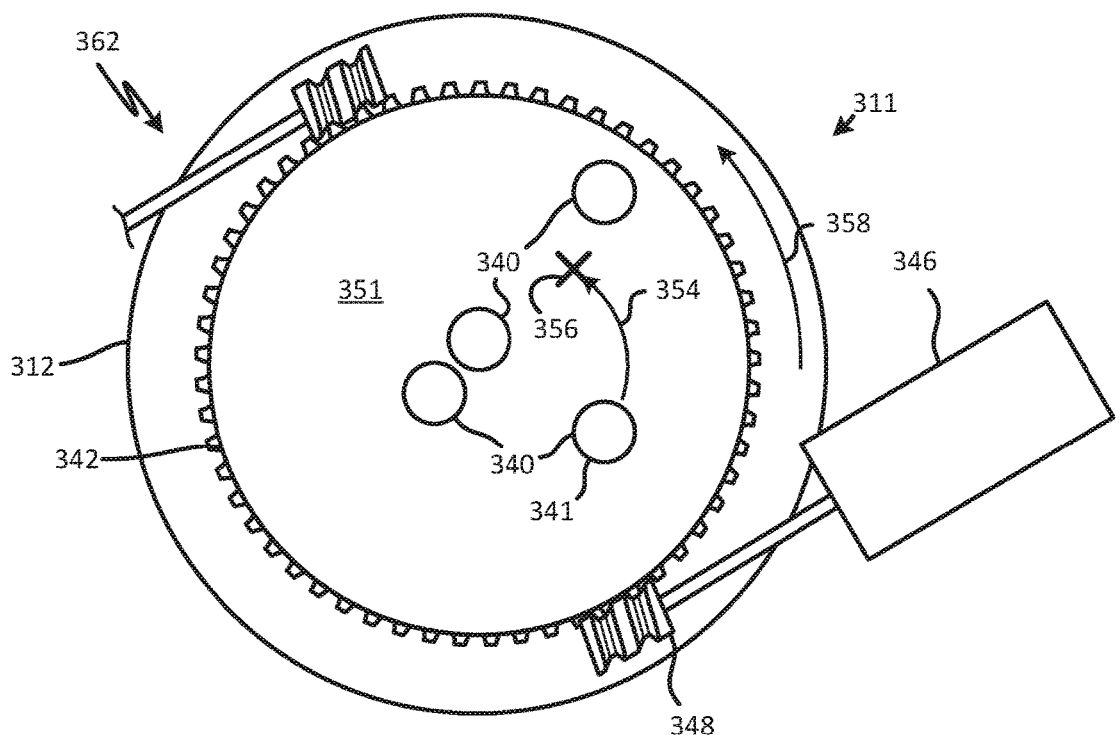
FIGS. 3J and 3K show another blood detector and blood access system according to embodiments of the disclosed subject matter.
Figure 3K:
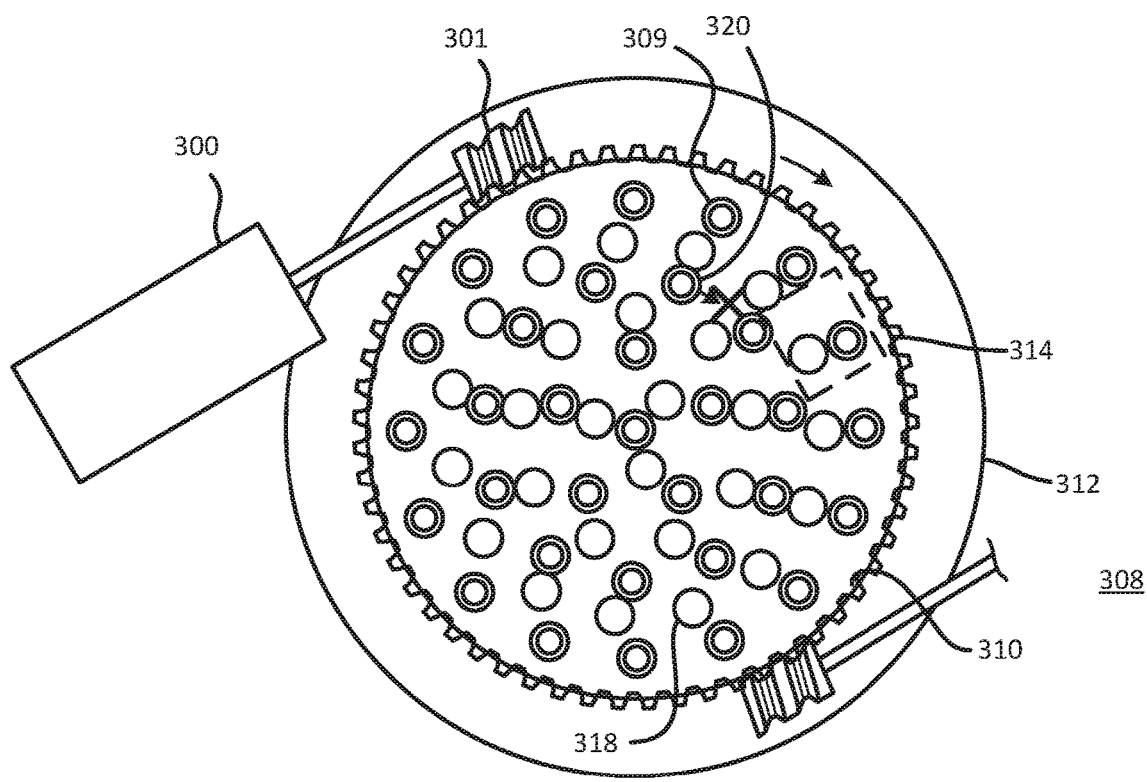

Referring now to FIGS. 3J and 3K, a blood extractor system according to another embodiment. Here a driving plate 351 has motors 311 (not shown but generally conforming the prior descriptions of motors for inserting the cannulae) located at the positions indicated at 340. In the present embodiment, instead of each cannula 309 being provided with its own motor 311. In the present embodiment, a motor 340 is provided for each ring of cannulae 309 such that when a target location is identified as described above, and the selected cannula 320 is positioned by rotating the plate 314 using the first motor 300. Then the driving plate 351 positioned to place a motor 340 at a radial position corresponding to the selected cannula over the selected cannula now at the target position. Then the controller can cause the motor 340 at the correct radial position to push the selected cannula as discussed above causing blood to be withdrawn.

Figure 3L:
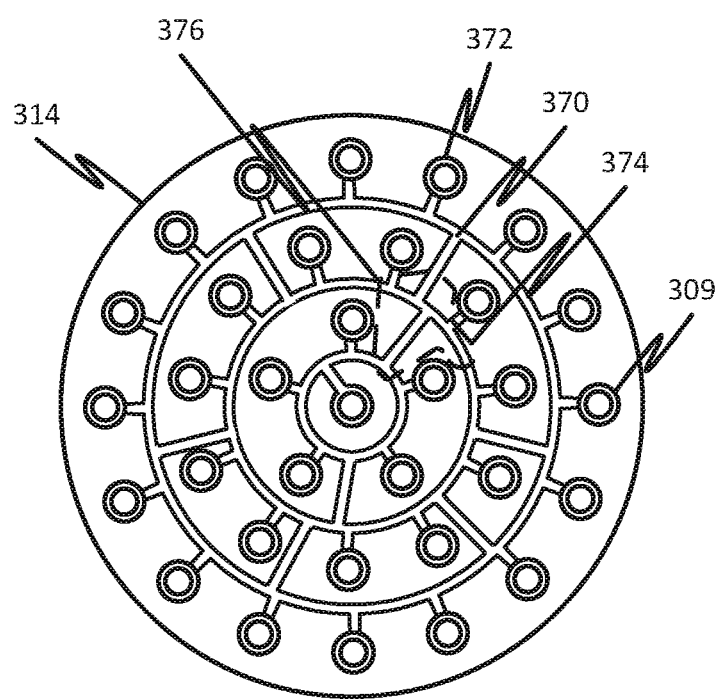
FIG. 3L shows a possible fluid circuit arrangement that may be used with any of the blood detector and access systems according to embodiments of the disclosed subject matter.

Referring to FIG. 3L, a network of channels 370 connect the cannulae 372 with the a port 374 which is connected to a sample chamber 376 which may be provided in the plate 314 or connected to the network and remote from the plate but movable therewith. The entire network may be maintained under vacuum, or placed under vacuum upon sampling, to permit the blood drawing function described above.

The embodiment of FIG. 3L is compatible with the foregoing embodiments of blood extractor systems. The sample chamber may also be provided in the plate 314 at a radial distance outside the outermost ring of cannulae. Note that the detectors 318 are not shown in the view of 3L for clarity but may be assumed present.

In variations of the above embodiments, there may be only one cannula for each radial position and the motor 300 may be rotated up to a greater angular distance (than earlier embodiments which had more than one cannula at each radial distance) in order to place the selected cannula at the position of the target location on the human or animal subject. Note also that in additional embodiments, a separate sample chamber may be provided for each cannula 309 rather employing a network of channels. In such a case, the end of the cannula may carry a chamber which is available for inspection after the sampling.

Referring to FIGS. 4A through 4D, a type of sample system that may be used to create a variation of the above-described blood extractor system embodiments. A first plate has bores, which may be cylindrical, running between opposite faces thereof as shown in FIG. 4E. Within each bore is an assembly that includes a spring 418, a cannula 412 with sharp tips 420 and 421 at each end supported by one or more supports such as disks 406 and 408. At least one support, in the present embodiment the disk 408, is positioned to compress the spring 418 thereby generating an urging force to maintain the cannula 412 spaced from an opening 416 where it access the human or animal subject. A shelf 417 may be provided to engage the end of the spring 418. Note instead of a spring an elastomer or stretch (rather than compression) spring may be used to create other embodiments. The sample chamber 404 may be made of material that can be punctured by the cannula tip 420 or may be provided with a septum that can be punctured. The sample chamber 404 may be provided with an internal vacuum which is retained for a storage life thereof. The sample chamber 404 also is provided with a permanent magnet 402. A rotatable drive plate 434 has permanent magnets 436 and 438 which can be positioned by rotating rotatable drive plate 434 relative to plate 314 to position a selected one of the permanent magnets 436 and 438 over the sample chamber 404 and its magnet 402 thereby determining whether the sample chamber is pulled toward the drive plate 434 or pushed away from it. When the drive plate 434 is in a first position, shown in FIG. 4A, a selected one of multiple cannulas 412 can be placed over a target in the manner described with respect to the foregoing embodiments. Then as indicated by the arrow 437 (FIG. 4C), the drive plate 434 can be rotated to position the magnet 436 over the sample chamber thereby forcing it downwardly as illustrated in FIG. 4D. This causes the cannula to pierce the sample chamber 404 and access it as well as causing the cannula to be driven downwardly to pierce the human or animal subject 449. The piercing of the sample chamber 404 causes the vacuum to be applied to the cannula 412 and thereby causes blood to be drawn therethrough and into the sample chamber 404. Once this process is completed, the plate 434, which may be part of a disposable, may be emplaced in an analysis unit (for example such as one described above with reference to FIGS. 1A to 1L) and the sampled blood analyzed in accord with the features and operations of the FIGS. 1A to 1L. In embodiments, the sample chamber may contain baffles or channels with reagent to cause activation and mixing of the sample fluid.

A drug delivery system, such as one for administration of insulin, may include a patch, all of which, or part of which, is disposable. The patch may be attachable to the body and have one or more micro-needles to provide access for infusion of a drug such as insulin. Further, the patch may contain a drug reservoir and a flow channel portion that engages with a pump. In embodiments, the pump has a disposable portion with the above elements and a non-disposable pump/controller portion with a pump/hardware unit that is connectable to the patch which has a pump, a motor, a battery, a wireless communications transceiver, and a controller, for example, a programmable controller including a microcomputer, memory, non-volatile data storage, and data interfaces. The controller may implement safety procedures. The controller may also implement procedures for maintaining predefined dosage and adjustments to drug dosage based on external commands from an external wireless device, such as a smartphone. The external device may monitor the operation of the patch and send commands to the pump/controller as well as receiving data from the pump/controller and storing, relaying, or displaying data responsively to the received data.

Figures 5A, 5B, 5C:
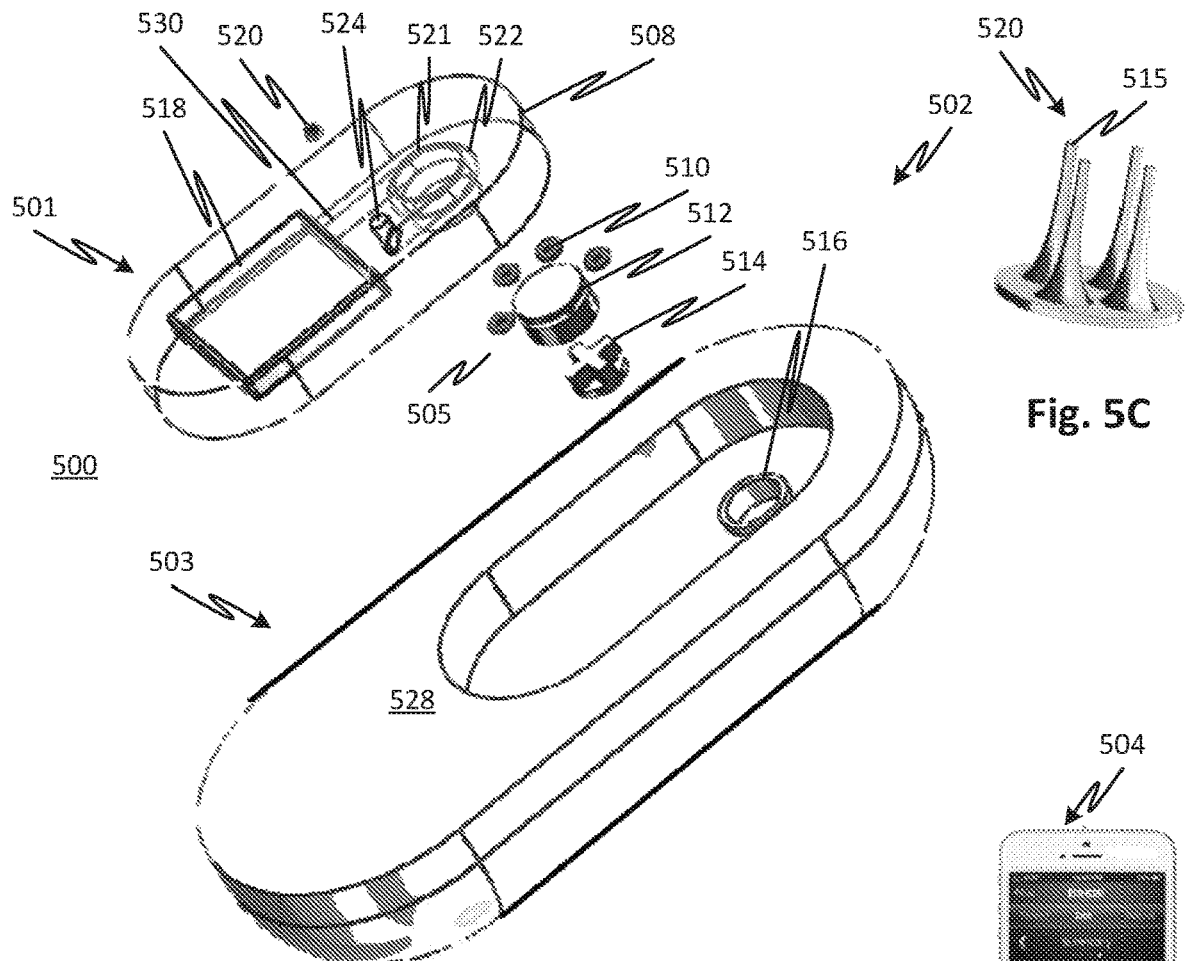
FIGS. 5A through 5C show a wearable drug delivery system according to embodiments of the disclosed subject matter.

In embodiments, the system comprises a drug patch with a disposable drug reservoir and access adapted to be worn on the body with the pump/controller attached thereto. Referring now to FIGS. 5A to 5C, a disposable portion of a patch (shown at 502 in an exploded view and with the pump controller portion 503 as an assembly ready (FIG. 5B) to be applied to the skin by adhesive attachment for example) has a disposable drug reservoir and access portion 508 and a permanent pump/controller portion 503 with a pump, controller and other components. The patch 500 disposable drug reservoir and access portion 508 includes a drug reservoir 518 and one or more hollow microneedles 520, which may be an array of microneedles. The microneedles 515 which, when the patch 500 is applied to the skin of a human or animal subject rests in or on top of the dermis. The disposable drug reservoir and access portion 508 drug reservoir 518 is connected by a tube 530 with a pumping portion 522 to a terminal end with the microneedle array 520. The pumping portion is exposed within a bore 521 of the disposable drug reservoir and access portion 508 frame allowing the rollers 510 of a peristaltic pump actuator 505. When the actuator 505 rotates, the contents of the drug reservoir 518 is progressively pumped to and out of the microneedles 515 of the microneedle array 520. The pump/controller 503 may include an electric motor to drive the actuator 505. The controller (not shown) controls the angular displacement of the pump rotor to output a predefined dose according to a current dosing schedule or under command from the external device 504. The disposable drug reservoir and access portion 508 may be packaged with a double-sided adhesive patch that is shaped to overlie the entire face of the pump/controller 503. The pump/controller 503 may include a power source such as replaceable or rechargeable battery or supercapacitor to provide power for the pump rotor 505 motor (not shown).

A separate pump/hardware unit operatively connects to the patch. It includes a pump element, which can be a reciprocating pump, a rotary pump, a peristaltic pump, a ratcheting pump, or the like. In one embodiment, a reusable peristaltic pump is provided for non-contact pumping to ensure sterility. The pump/hardware unit also comprises a rechargeable battery, a pump motor, safety sensors to detect occlusion, temperature, low reservoir volume, etc., an alert system, and a data communication device such as a Bluetooth chip.

The system can be connected via the data communication device to a controller for adjusting drug dosage. The controller also receives data regarding status and sensor information from the pump/hardware unit. The controller can also include an instruments such as a glucometer with a self-contained drum of 10-15 sets of needles/lancets and test strips. An external device, such as a smartphone, can act as a server to send commands to the controller (e.g., to set basal and bolus dosage profiles which can be based on information received by the external device). Thus, the external device can continuously obtain data from the controller and/or the pump/hardware unit, perform analysis, make dosage recommendations, send reminders, etc. to the user.

The disclosed drug delivery system can be used, for example, to deliver insulin. It is portable, easy to use and wear, and reduces medical waste because most of it is reusable. It also enables convenient and accurate dosage control and monitoring via the smartphone controller. In certain embodiments, a glucometer can be integrated with the pump/hardware unit, and send glucose data to the controller for dosage determination. Alternatively, a separate glucometer can send data to the controller wirelessly.

Other disclosed embodiments include a microneedle patch for interstitial fluid sampling. In this embodiment, a patch to be placed against the skin has microneedles that swell and capture interstitial fluid like a sponge. The microneedles can contain integrated sensors or portions of sensors such as reagents that are expended over time and whose interaction with biological fluid is revealed by phosphorescence or fluorescence (the latter employing a light source in the patch 500). Since the probe height of the needles is fixed, interstitial fluid sampling is ensured. The patch 500 can sample at a controlled rate, and can sense continuously. With a single array of microneedles, multiple sensors placed on separate sampling sites can accurately measure multiple parameters. Signals from the sensors can be transmitted to an electronic device for processing, via wires or wirelessly, thereby enabling monitoring of chronic diseases such as diabetes, as well as monitoring of continuous activities such as exercise and sleep.

Figures 6A, 6B, 6C:
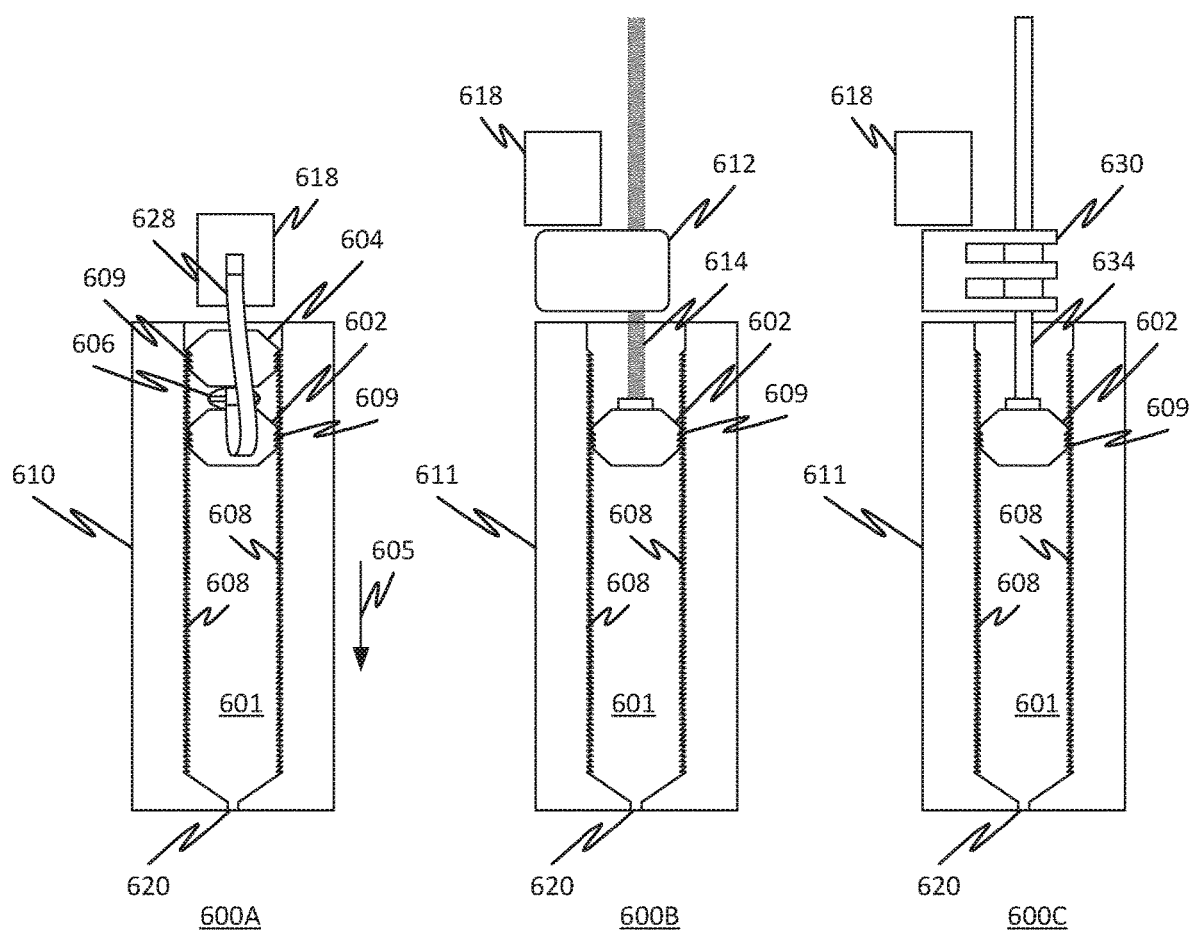
FIGS. 6A through 6C show a pump mechanism that may be used with the embodiments of FIG. 5A through 5C or other devices, according to embodiments of the disclosed subject matter.

Referring now to FIG. 6A, a pump system 600A that may be used with the patch 500 system described above may employ a disposable pump unit 600A with a piston 602 and pusher 604 arranged in a cylinder within a frame 610. The piston 602 and pusher 604 engage with angled teeth 608 to form a ratchet arrangement whose resistance to movement of the piston 602 and pusher 604 in the downward direction (indicated by arrow 605) is lower than that in the upward direction. A piezoelectric spreader 606 is positioned and connected to urge piezoelectric spreader 606 apart and then recoils to urge the piston 602 and pusher 604 together with the result that the piston 602 is pushed down in an incremental crawling fashion, each step being selected to deliver a predefined quantity of fluid stored in the cylinder 601 and conveyed through the port 620. A drive circuit 618 may be connected to the piezoelectric spreader 606 by a flexible cable 628 or by a conductor and brush arrangement (not shown) or any other suitable mechanism. The drive circuit 618 may generate controlling current pulses that determine the number of steps to be displaced by the piston 602 and pusher 604 thereby to determine the dosing. Thus, the drive circuit 618 can be the final controller of the remote control device 504 to determine the administration of drug or medicament or other material. A benefit of the ratcheting-type mechanism is that the system prevents backflow of fluid into the drug administration flow path which could cause fouling or contamination. A second benefit is that if occlusion occurs, the positive volume "stop" will generate a stronger pressure pulse than a more compliant system which can facilitate detection of the occlusion by a pressure sensor in fluid communication with the cylinder 601.

Referring now to FIG. 6B, a further pump system 600B that may be used with the patch 500 system described above may employ a disposable pump unit 600A with a piston 602 and linear drive 612 that turns a nut (within and not shown) in threading engagement with a lead screw 164 thereby to push the piston 602 within the cylinder 601 within the frame 610. The piston 602 engages with angled teeth 608 to form a ratchet arrangement whose resistance to movement of the piston 602 in the downward direction (indicated by arrow 605) is lower than that in the upward direction. As the piston is urged downwardly by the lead screw 614, it seeks preferred positions and locks there until the lead screw overcomes the resistance—forming a détente mechanism. Each step is selected to deliver a predefined quantity of fluid stored in the cylinder 601 and conveyed through the port 620. The drive circuit 618 may be connected to linear drive 612 and generate controlled current pulses that determine the number of steps to be displaced by the piston 602 thereby to determine the dosing. Thus, the drive circuit 618 can be the final controller of the remote control device 504 to determine the administration of drug or medicament or other material. As before, the benefit of this kind of ratcheting mechanism is that the system prevents backflow of fluid into the drug administration flow path which could cause fouling or contamination. A second benefit is that if occlusion occurs, the positive volume "stop" will generate a stronger pressure pulse than a more compliant system which can facilitate detection of the occlusion by a pressure sensor in fluid communication with the cylinder 601. The embodiment 600C of FIG. 6C is similar to the embodiment 600B of FIG. 6B except that instead of a linear drive 630 that turns a nut to push a lead screw, an inchworm-type piezoelectric motor 630 applies downward thrust to a smooth rod 634 to push the piston 602.

In any of the embodiments of FIGS. 6A through 6C, the drive circuit 618 may be incorporated in a pump/controller portion such as 503. In further embodiments, the linear drive 612 or 630 may be incorporated in the pump/controller portion. In further embodiments, the lead screw 614 or rod 634 is incorporated in the pump/controller portion. Suitable electrical contacts may be provided to electrically connect a disposable motor with a power source in the pump/controller portion, for example contacts at the end of cable 628 for example.

In any of the embodiments employing a foam layer, a solid material such as flexible synthetic or natural elastomer may also be used. In any of the embodiments in which permanent magnets are used to create a selectable force, one or a pair of permanent magnets can be replaced with an electromagnet to perform the selection function by reversing current or turning it on or off in order to displace the sample chamber and push the cannula as described. In any of the embodiments describing a plate, the plate can be an open truss structure or any structure suitable for carrying the identified elements.

According to first embodiments, the disclosed subject matter includes a system for transdermal fluid extraction from a subject. The system includes one or more microneedles; a rotary pump coupled to the one or more microneedles; and one or more collection chambers. The rotary pump is configured to convey fluid from the subject through the one or more microneedles to the one or more collection chambers. The rotary pump includes a cylinder-and-piston set attached between an inner track and an outer track. The inner track is nested within the outer track. The inner track is connected to rotate eccentrically with the outer track. A distal end of the piston of the cylinder-and-piston set is movably engageable with the outer track. A first end of the cylinder of the piston-and-cylinder set is movably engageable with the inner track and operatively connected to the one or more microneedles such that rotation of the piston-and-cylinder set relative to the inner and outer tracks is convertible to motion of the piston inside the cylinder and a pressure difference generated by the motion of the piston is transmitted to the one or more microneedles to drive the fluid through the one or more microneedles.

The first embodiments may be modified to form additional first embodiments, in which when a proximal end of the piston opposite the distal end of the piston is disposed at the proximal end of the cylinder, and the piston-and-cylinder set is rotated, fluid is extracted from the subject in an extraction mode; and wherein when the proximal end of the piston is disposed near a distal end of the cylinder opposite the proximal end of the cylinder, and the piston-and-cylinder set is rotated, fluid is collected in the one or more collection chambers in a collection mode. The first embodiments may be modified to form additional first embodiments, in which the outer track comprises a vertical cylindrical wall, and the inner track comprises the periphery of a circular shaft fixed relative to the vertical cylindrical wall; wherein the distal end of the piston is movably engageable with a groove in the outer track, and the proximal end of the cylinder is attached to a cylindrical sleeve rotatable around the circular shaft.

The first embodiments may be modified to form additional first embodiments, in which the sleeve is slidable on the shaft; wherein the vertical cylindrical wall has a bottom surface, and the groove in the outer track varies in distance from the bottom surface, such that the sleeve correspondingly slides on the shaft as the piston-and-cylinder set is rotated; wherein the one or more micro-needles is a circular array of micro-needles surrounding the shaft and attached to the sleeve; and wherein the groove in the outer track varies in distance from the bottom surface of the vertical cylindrical wall such that an end of the shaft selectively protrudes beyond the end of the microneedle array to prevent contact of the microneedle array with the skin of the subject during the collection mode.

The first embodiments may be modified to form additional first embodiments, in which the one or more collection chambers are included in a collection chip. The first embodiments may be modified to form additional first embodiments, in which the one or more collection chambers include anti-coagulants. The first embodiments may be modified to form additional first embodiments, that include one or more sensors configured to detect blood in the collection chambers. The first embodiments may be modified to form additional first embodiments, that include a detector for analyzing the collected fluid. A method for transdermal fluid extraction from a subject comprising applying the system of any of claims 1-8 to extract fluid through the skin of the subject. The first embodiments may be modified to form additional first embodiments, that include the fluid is blood, and the extraction of blood is from a vein of the human or animal subject.

According to second embodiments, the disclosed subject matter includes a drug delivery system comprising: a patch attachable to the skin of a subject. The patch includes one or more micro-needles and a drug reservoir. The system includes a pump unit removably attachable to the patch. The pump unit has a pump for pumping a drug from the drug reservoir through the one or more micro-needles to the subject. A wireless communication device is operatively connected to the pump. A controller wirelessly communicates with the wireless communication device of the pump unit for controlling the pump unit to deliver a predetermined dosage of the drug to the subject.

The second embodiments may be modified to form additional second embodiments, in which the patch is disposable. The second embodiments may be modified to form additional second embodiments, in which the one or more microneedles includes an array of four microneedles. The second embodiments may be modified to form additional second embodiments, in which the pump unit comprises a motor operatively connected to the pump, and a battery for powering the motor. The second embodiments may be modified to form additional second embodiments, in which the pump unit comprises a safety-related sensor, and the wireless communication device is for sending data from the safety-related sensor to the controller. The second embodiments may be modified to form additional second embodiments, in which the safety-related sensor comprises at least one sensor for detecting at least one of an occlusion, a drug volume in the reservoir, and a temperature of the drug. The second embodiments may be modified to form additional second embodiments, in which the safety-related sensor is for monitoring the operation of the pump. The second embodiments may be modified to form additional second embodiments, in which the pump unit comprises an alert system for alerting the subject to at least one of a malfunction of the drug delivery system, a mode of operation of the drug delivery system, and a message regarding maintenance of the drug delivery system. The second embodiments may be modified to form additional second embodiments, in which the pump is one of a peristaltic pump, a reciprocating pump, or a syringe pump. The second embodiments may be modified to form additional second embodiments, in which the drug reservoir comprises a unidirectional self-locking plunger for forcing a predetermined amount of the drug out of the reservoir and through the one or more microneedles; and wherein the pump unit includes a cam and a motor for driving the cam for engaging the plunger to move the plunger to force the drug out of the reservoir. The second embodiments may be modified to form additional second embodiments, in which the reservoir comprises opposing ribbed walls, and the plunger is shaped for cooperating with the ribbed walls to form a ratcheting mechanism allowing the plunger to move in only one direction in the reservoir to force the predetermined amount of the drug out of the reservoir. The second embodiments may be modified to form additional second embodiments, in which the pump unit comprises a manual control panel for operating the pump. The second embodiments may be modified to form additional second embodiments, in which the controller comprises a data processor for receiving the data from the safety-related sensor of the pump unit and calculating the predetermined dosage of the drug based on the safety-related sensor data. The second embodiments may be modified to form additional second embodiments, in which the controller comprises a glucometer, and the data processor of the controller calculates the predetermined dosage of the drug using data from the glucometer. The second embodiments may be modified to form additional second embodiments, that include a remote data processing device for wirelessly communicating with the controller and with the wireless communication device of the pump unit for receiving data from the controller and the pump unit, and for controlling the pump unit to deliver the predetermined dosage of the drug based on the received data. The second embodiments may be modified to form additional second embodiments, in which the received data includes dosage control data from the controller, and data from safety-related sensors of the pump unit. The second embodiments may be modified to form additional second embodiments, in which the remote data processing device is for storing and logging the received data. The second embodiments may be modified to form additional second embodiments, in which the remote data processing device is for recommending a dosage of the drug to the subject based on the received data. The system of any one of claims 25 to 28, as filed, wherein the remote data processing device is for calculating at least one of a basal dosage and a bolus dosage of the drug. The second embodiments may be modified to form additional second embodiments, in which the remote data processing device is for generating reminders to the subject regarding at least one of a scheduled bolus dosage and a scheduled blood glucose test. The second embodiments may be modified to form additional second embodiments, in which the remote data processing device is for determining at least one of a maximum dosage and a maximum dosage frequency of the drug based on the received data. The second embodiments may be modified to form additional second embodiments, in which the remote data processing device is for calculating nutritional guidelines for the subject based on the received data. The second embodiments may be modified to form additional second embodiments, in which the remote data processing device comprises a smartphone.

According to third embodiments, the disclosed subject matter includes a system for extracting blood from a vein of a subject. The system has one or more microneedles and an array of photodetectors to determine the location of the vein for the extraction of blood. A motor is operatively connected to the one or more microneedles to move the micro-needles. A controller processes a signal from the array of photodetectors and operates the motor to move a selected microneedle of the one or more microneedles to the location of the vein for the extraction of blood.

The third embodiments may be modified to form additional third embodiments, in which the selected microneedle is selected based on its proximity to the determined location of the vein. The third embodiments may be modified to form additional third embodiments, that include a housing for mounting the one or more microneedles, the motor, the array of photodetectors, and the controller. The third embodiments may be modified to form additional third embodiments, in which the housing is adapted to be placed on the skin of the subject such that the one or more microneedles and the photodetector array face the skin but do not contact the skin; the system further includes an actuator for pushing the selected microneedle into the vein and the controller is configured to operate the actuator to push the selected microneedle into the vein after the selected microneedle is moved to the location of the vein. The third embodiments may be modified to form additional third embodiments, in which the actuator is movably mounted, the system comprising an actuator motor for moving the actuator to a position corresponding to the selected microneedle responsive to the controller.

The third embodiments may be modified to form additional third embodiments, in which the one or more microneedles and the photodetector array are mounted on a first rotatable base, and the motor and controller are for causing the first rotatable base to rotate to move the selected microneedle to the location of the vein The third embodiments may be modified to form additional third embodiments, in which the first rotatable base is ring-shaped, the system comprising a ring-shaped second rotatable base concentric with the first rotatable base, the second rotatable base has one or more microneedles and a photodetector array, and a second motor for causing the second rotatable base to rotate; wherein the controller is for processing signals from the arrays of photodetectors of the first and second rotatable bases, for selecting the selected microneedle from the first and second rotatable bases, and for operating the motors to move the selected microneedle to the location of the vein.

The third embodiments may be modified to form additional third embodiments, in which the one or more microneedles each are slidably mounted in the housing and biased to a retracted position away from the subject's skin, and has a first end facing the subject's skin and a second end facing into the housing, and wherein the actuator comprises an electromagnet has a permanent magnet fixedly mounted in the housing above the second end of the selected microneedle, and a sample storage unit movably mounted between the second end and the electromagnet, the sample storage unit has a puncturable/sealable membrane maintaining a vacuum in the sample storage unit; wherein in a non-sampling state, the permanent magnet of the electromagnet magnetically attracts the sample storage unit, and in a sampling state the electromagnet receives a signal from the controller for causing the electromagnet to repel the sample storage unit; wherein in the sampling state the sample storage unit is pushed against the selected microneedle to push the selected microneedle into the vein and puncture the membrane, whereby the vacuum draws blood through the needle and into the sample storage unit. The third embodiments may be modified to form additional third embodiments, in which the controller is for removing the signal from the electromagnet after the blood is drawn into the sample storage unit; wherein each of the one or more microneedles has a spring for biasing the microneedle to the retracted position, and for returning the selected microneedle to the retracted position when the electromagnet is switched from the sampling state to the non-sampling state by the controller. The third embodiments may be modified to form additional third embodiments, in which an interior of the sample storage unit has a coating of an anticoagulant. The system of any one of claims 34 to 43, as filed, wherein the photodetectors are for detecting infrared light, the system comprising an infrared light source.

According to fourth embodiments, the disclosed subject matter includes a system for transdermal extraction of interstitial fluid from a subject. The system includes one or more microneedles, a sensor attached to the one or more microneedles for sensing the interstitial fluid and a substrate for mounting the sensor such that when the substrate is in contact with the skin of the subject, the one or more microneedles probe the skin to extract the interstitial fluid.

The fourth embodiments may be modified to form additional fourth embodiments, in which the one or more microneedles comprise a polymer to absorb and extract the interstitial fluid. The fourth embodiments may be modified to form additional fourth embodiments, that include a plurality of sensors mounted to the substrate, each sensor attached to one or more of the microneedles. The fourth embodiments may be modified to form additional fourth embodiments, that include a communication device for transmitting a signal from the sensor.

According to fifth embodiments, the disclosed subject matter includes a drug administration system, comprising: a disposable kit includes an adhesive tape with adhesive on both sides attachable to a predefined powered unit and the skin of a human or animal subject and a cartridge that includes a patient access device. A drug reservoir is prefilled with a drug. A pumping channel is connects the drug reservoir with the patient access device. The predefined powered unit includes a wireless transceiver, a pump, a power source, and a controller programmed to receive dosing data from a wireless smart device and to implement a dosing schedule. The predefined powered unit is shaped to be attachable by means of said adhesive tape to a human or animal subject to position the cartridge adjacent to the human or animal subject; the cartridge is shaped such that it engages with a receiving portion of the predefined powered unit and upon engaging, the pumping channel engages with a pump actuator of the pump; the controller is further programmed to operate the pump according to the dosing schedules received from the wireless smart device.

The fifth embodiments may be modified to form additional fifth embodiments, that include the wireless smart device. The wireless smart device is connectable to a network or the Internet and is further provided with an application that generates the dosing schedule according to rules received from a server over said network or Internet. The fifth embodiments may be modified to form additional fifth embodiments, in which the patient access device includes at least one microneedle. The fifth embodiments may be modified to form additional fifth embodiments, in which the at least one microneedle has a length, and the cartridge and powered unit are configured such that when the powered unit is adhesively attached to the human or animal subject, the tip of the at least one microneedle rests at or just below the outermost part of the dermis of the human or animal host. The fifth embodiments may be modified to form additional fifth embodiments, in which the at least one microneedle has a length, and the cartridge and powered unit are configured such that when the powered unit is adhesively attached to the human or animal subject, the tip of the at least one microneedle rests at a point in the skin of the human or animal host that is effective to prevent bleeding. The fifth embodiments may be modified to form additional fifth embodiments, in which the pumping channel is a tube and the pumping actuator includes a peristaltic pump rotor.

According to sixth embodiments, the disclosed subject matter includes a drug administration system. A disposable kit includes an adhesive tape with adhesive on both sides attachable to a predefined powered unit and the skin of a human or animal subject and a cartridge that includes a patient access device, a drug reservoir prefilled with a drug, a pump configured to pump fluid from the drug reservoir to the patient access device. The predefined powered unit includes a wireless transceiver, a power source, and a controller programmed to receive dosing data from a wireless smart device and to implement a dosing schedule. The predefined powered unit is shaped to be attachable by means of said adhesive tape to a human or animal subject to position the cartridge adjacent to the human or animal subject. The cartridge is shaped such that it engages with a receiving portion of the predefined powered unit and upon engaging, the pump is connected to a power source or mechanical actuator of the powered unit. The controller is further programmed to operate the pump according to the dosing schedules received from the wireless smart device.

The sixth embodiments may be modified to form additional sixth embodiments, that include the wireless smart device, the wireless smart device is connectable to a network or the Internet and is further provided with an application that generates the dosing schedule according to rules received from a server over said network or Internet. The sixth embodiments may be modified to form additional sixth embodiments, in which the patient access device includes at least one microneedle. The sixth embodiments may be modified to form additional sixth embodiments, in which the at least one microneedle has a length, and the cartridge and powered unit are configured such that when the powered unit is adhesively attached to the human or animal subject, the tip of the at least one microneedle rests at or just below the outermost part of the dermis of the human or animal host. The sixth embodiments may be modified to form additional sixth embodiments, in which the at least one microneedle has a length, and the cartridge and powered unit are configured such that when the powered unit is adhesively attached to the human or animal subject, the tip of the at least one microneedle rests at a point in the skin of the human or animal host that is effective to prevent bleeding. The sixth embodiments may be modified to form additional sixth embodiments, in which the pump includes a piston with teeth that engage the wall of a cylinder in which the piston is placed such that the piston is located at discrete stops defining increments of a dose of a drug contained in the cylinder. The sixth embodiments may be modified to form additional sixth embodiments, in which the piston is attached to a piezoelectric motor The sixth embodiments may be modified to form additional sixth embodiments, in which the cartridge or the powered unit includes a linear drive.

According to seventh embodiments, the disclosed subject matter includes a system for sampling fluid from a human or animal subject. A first member has at least one sample chamber storing a vacuum, the at least one sample chamber carrying a permanent magnet affixed thereto. A second member is movable relative to the first, and carries permanent magnets in opposite relative orientations. A cannula has sharp open ends and is disposed adjacent said sample chamber. A controller is configured to move the first member relative to the second member to switch between a first configuration in which the sample chamber is biased away from the cannula and second configuration in which a magnetic force causes the sample chamber to be biased toward the cannula such that it is pierced thereby and applies a vacuum to one end of the cannula.

The seventh embodiments may be modified to form additional seventh embodiments, in which the bias of the sample chamber toward the sample chamber causes the cannula to be interferingly engaged with sample chamber thereby causing it to move such that a human or animal subject positioned in a predetermined position relative to the second member is pierced by the cannula. The seventh embodiments may be modified to form additional seventh embodiments, in which a bias member is positioned adjacent the cannula opposite an interfering element attached to the cannula to maintain a position of the cannula until the sample chamber biases it such that the cannula can pierce the human or animal subject. The seventh embodiments may be modified to form additional seventh embodiments, in which the first member contains multiple pairs of magnets arranged to bias multiple sample chambers selectively under control of a controller. The seventh embodiments may be modified to form additional seventh embodiments, that include at least one motor drive adapted to move the first and second members, wherein the at least one motor drive is configured to move the second member to move a selected one of multiple cannulae to a target position over the skin of a human or animal subject. The seventh embodiments may be modified to form additional seventh embodiments, that include at least one motor drive adapted to move the first and second members, the second member includes an array of detectors configured to indicate hemoglobin concentration in the tissues of a human or animal subject and wherein the at least one motor drive is configured to move the second member to move a selected one of multiple cannulae to a target position over the skin of a human or animal subject responsively to signals from said detectors.

According to eighth embodiments, the disclosed subject matter includes a system for extracting fluid from a patient. A first member is attached to a sample chamber and a bodily fluid access device. The system includes at least one pump. The first member is shaped and sized to be positioned against a body part of a human or animal subject. A second member is pivotably attached to the first member and has a cam surface that engages the at least one pump to move the access device and actuate the pump to perform a sample extraction by generating a vacuum applied to the bodily fluid access device, the cam surface is further shaped such that it applies a force to the access device to move the access device first in a first direction and then in a second direction such that the access member moves in the first direction and is displaced so as to pierce a human or animal subject positioned against the first member and moves in the second direction and is removed from a human or animal subject positioned against the first member. The eighth embodiments may be modified to form additional eighth embodiments, in which the cam surface is defined along a cylindrical surface whose axis is perpendicular to a surface that engages a human or animal subject. The eighth embodiments may be modified to form additional eighth embodiments, in which the second member is cylindrical and is connected at a point that is eccentric with respect to an axis thereof.

According to ninth embodiments, the disclosed subject matter includes a device for sampling fluid. A first member has an array of microneedles. Arranged coplanar with the first member is an array of detectors. The optical detectors are adapted to detect hemoglobin in the body of a human or animal subject. A controller is adapted to receive signals from the detectors and to calculate a position for insertion of an extraction needle responsively to the detector signals, either by itself or by conveying data to a remote computation device. A drive motor is arranged to move the first member to position a selected one of the microneedles responsively to said position for insertion. The system includes a mechanism for translating the selected one of the microneedles along an axis thereof such that the selected one of microneedles can be inserted in a human or animal subject. The ninth embodiments may be modified to form additional ninth embodiments, that include a housing enclosing at least the first member and fitted with a retaining strap to permit the housing to be strapped to a human or animal subject. The ninth embodiments may be modified to form additional ninth embodiments, in which the first member is fitted with an extraction motor arranged to move the selected one of the microneedles along an axis thereof. The ninth embodiments may be modified to form additional ninth embodiments, that include a second member, movable relative to the first, and carrying an extraction motor arranged to move the selected one of the microneedles along an axis thereof. The ninth embodiments may be modified to form additional ninth embodiments, in which the extraction motor is one of a linear motor and a thermoelectric motor. The ninth embodiments may be modified to form additional ninth embodiments, in which the first member includes a network of channels and a sample chamber held under vacuum. The ninth embodiments may be modified to form additional ninth embodiments, that include an infrared light source, wherein the first member includes a light guide shaped to output light at various points of an external surface coinciding with detectors of said array of detectors.

Embodiments of a method, system and computer program product for biological fluid extraction and drug delivery may be implemented on a general-purpose computer, a special-purpose computer, a programmed microprocessor or microcontroller and peripheral integrated circuit element, an ASIC or other integrated circuit, a digital signal processor, a hardwired electronic or logic circuit such as a discrete element circuit, a programmed logic device such as a PLD, PLA, FPGA, PAL, or the like. In general, any process capable of implementing the functions or steps described herein can be used to implement embodiments of the method, system, or computer program product for biological fluid extraction and drug delivery.

Furthermore, embodiments of the disclosed method, system, and computer program product for biological fluid extraction and drug delivery may be readily implemented, fully or partially, in software using, for example, object or object-oriented software development environments that provide portable source code that can be used on a variety of computer platforms. Alternatively, embodiments of the disclosed method, system, and computer program product for biological fluid extraction and drug delivery can be implemented partially or fully in hardware using, for example, standard logic circuits or a VLSI design. Other hardware or software can be used to implement embodiments depending on the speed and/or efficiency requirements of the systems, the particular function, and/or a particular software or hardware system, microprocessor, or microcomputer system being utilized. Embodiments of the method, system, and computer program product for biological fluid extraction and drug delivery can be implemented in hardware and/or software using any known or later developed systems or structures, devices and/or software by those of ordinary skill in the applicable art from the functional description provided herein and with a general basic knowledge of the computer, exhaust and fluid flow, and/or cooking appliance arts.

Moreover, embodiments of the disclosed method, system, and computer program product for biological fluid extraction and drug delivery can be implemented in software executed on a programmed general-purpose computer, a special purpose computer, a microprocessor, or the like. Also, the biological fluid extraction and drug delivery method of this invention can be implemented as a program embedded on a personal computer such as a JAVA® or CGI script, as a resource residing on a server or graphics workstation, as a routine embedded in a dedicated processing system, or the like. The method and system can also be implemented by physically incorporating the method for controlling a cold water spray system into a software and/or hardware system, such as the hardware and software systems of biological fluid extraction and drug delivery.

It is, therefore, apparent that there is provided in accordance with the present invention, a method, system, and computer program product for biological fluid extraction and drug delivery. While this invention has been described in conjunction with a number of embodiments, it is evident that many alternatives, modifications and variations would be or are apparent to those of ordinary skill in the applicable arts. Accordingly, applicants intend to embrace all such alternatives, modifications, equivalents and variations that are within the spirit and scope of this invention.

What is claimed is:

1. A device for sampling fluid, comprising:
a first member having an array of microneedles and, coplanar therewith, an array of optical detectors, optical detectors of said array of optical detectors being adapted to detect hemoglobin in the body of a human or animal subject;
a controller configured to receive signals from the detectors and to calculate a position for insertion of a selected one of the microneedle responsively to the detector signals, the controller being configured to calculate said position either by itself or by conveying data to a remote computation device;
a drive motor arranged to move the first member to position the selected one of the microneedles responsively to said position for insertion;
a mechanism constructed to translate the selected one of the microneedles along an axis thereof such that the selected one of microneedles can be inserted in a human or animal subject.

2. The device of claim 1, further comprising a housing enclosing at least the first member and fitted with a retaining strap to permit the housing to be strapped to a human or animal subject.

3. The device of claim 1, wherein the first member is fitted with an extraction motor arranged to move the selected one of the microneedles along an axis thereof.

4. The device of claim 1, further comprising a second member, movable relative to the first, and carrying an extraction motor arranged to move the selected one of the microneedles along an axis thereof.

5. The device of claim 3, wherein the extraction motor is one of a linear motor and a thermoelectric motor.

6. The device of claim 1, where in the first member includes a network of channels and a sample chamber held under vacuum.

7. The device of claim 1, further comprising an infrared light source, wherein the first member includes a light guide shaped to output light at various points of an external surface coinciding with detectors of said array of detectors.

8. A system for extracting blood from a vein of a subject, the system comprising: one or more microneedles;
an array of photodetectors to determine the location of the vein for the extraction of blood;
a motor operatively connected to the one or more microneedles to move the micro-needles; and
a controller configured to process a signal from the array of photodetectors and to operate the motor to move a selected microneedle of the one or more microneedles to the location of the vein for the extraction of blood;
a housing for mounting the one or more microneedles, the motor, the array of photodetectors, and the controller;
wherein the housing is constructed to be placed on the skin of the subject such that the one or more microneedles and the photodetector array face the skin but do not contact the skin;
the system further comprising an actuator for pushing the selected microneedle into the vein;
wherein the controller is configured to operate the actuator to push the selected microneedle into the vein after the selected microneedle is moved to the location of the vein.

9. The system of claim 8, wherein the selected microneedle is selected based on its proximity to the determined location of the vein.

10. The system of claim 8, wherein the actuator is movably mounted, the system comprising an actuator motor that moves the actuator to a position corresponding to the selected microneedle responsive to the controller.

11. The system of claim 8, wherein the one or more microneedles and the photodetector array are mounted on a first rotatable base, and the motor and controller are configured to cause the first rotatable base to rotate to move the selected microneedle to the location of the vein.

12. The system of claim 11, wherein the first rotatable base is ring-shaped, the system comprising a ring-shaped second rotatable base concentric with the first rotatable base, the second rotatable base having one or more microneedles and a photodetector array, and a second motor that rotates the second rotatable base;
wherein the controller is configured to process signals from the arrays of photodetectors of the first and second rotatable bases, to select the selected microneedle from the first and second rotatable bases, and to operate the motors to move the selected microneedle to the location of the vein.

13. The system of claim 8, wherein the one or more microneedles each are slidably mounted in the housing and biased to a retracted position away from the subject's skin, and has a first end facing the subject's skin and a second end facing into the housing, and
wherein the actuator comprises an electromagnet having a permanent magnet fixedly mounted in the housing above the second end of the selected microneedle, and a sample storage unit movably mounted between the second end and the electromagnet, the sample storage unit having a puncturable/sealable membrane maintaining a vacuum in the sample storage unit;
wherein in a non-sampling state, the permanent magnet of the electromagnet magnetically attracts the sample storage unit, and in a sampling state the electromagnet receives a signal from the controller for causing the electromagnet to repel the sample storage unit;
wherein in the sampling state, the sample storage unit is pushed against the selected microneedle to push the selected microneedle into the vein and puncture the membrane, whereby the vacuum draws blood through the needle and into the sample storage unit.

14. The system of claim 13, wherein the controller is configured to remove the signal from the electromagnet after the blood is drawn into the sample storage unit;
wherein each of the one or more microneedles has a spring for biasing the microneedle to the retracted position, and for returning the selected microneedle to the retracted position when the electromagnet is switched from the sampling state to the non-sampling state by the controller.

15. The system of claim 13, wherein an interior of the sample storage unit has a coating of an anticoagulant.

16. The system of claim 8, wherein the photodetectors detect infrared light, and the system comprises an infrared light source.

17. A device for sampling fluid, comprising:
a first member having an array of microneedles and an array of optical detectors, optical detectors of said array of optical detectors being constructed to detect hemoglobin in the body of a human or animal subject;
a controller configured to receive signals from the detectors and to calculate a position for insertion of a selected one of the microneedle responsively to the detector signals, the controller being configured to calculate said position either by itself or by receiving said position from a remote computation device;

a drive motor arranged to move the first member to position the selected one of the microneedles responsively to said position for insertion;

a mechanism for translating the selected one of the microneedles along an axis thereof such that the selected one of microneedles can be inserted in a human or animal subject.

18. The device of claim 17, further comprising a housing enclosing at least the first member and fitted with a retaining strap to permit the housing to be strapped to a human or animal subject.

19. The device of claim 17, wherein the first member is fitted with an extraction motor constructed to move the selected one of the microneedles along an axis thereof.

20. The device of claim 17, further comprising a second member, movable relative to the first, and carrying an extraction motor constructed to move the selected one of the microneedles along an axis thereof.

21. The device of claim 19, wherein the extraction motor is one of a linear motor and a thermoelectric motor.

22. The device of claim 17, wherein the first member includes a network of channels and a sample chamber held under vacuum.

23. The device of claim 17, further comprising an infrared light source, wherein the first member includes a light guide shaped to output light at various points of an external surface coinciding with detectors of said array of optical detectors.

* * * * *